US011837366B2

(12) United States Patent
Fazio et al.

(10) Patent No.: US 11,837,366 B2
(45) Date of Patent: Dec. 5, 2023

(54) INFECTION RISK PREDICTION

(71) Applicant: ACCENTURE GLOBAL SOLUTIONS LIMITED, Dublin (IE)

(72) Inventors: Robi Fazio, Le Cannet (FR); Christian Souche, Cannes (FR); Alexandre Naressi, Valbonne (FR)

(73) Assignee: ACCENTURE GLOBAL SOLUTIONS LIMITED, Dublin (IE)

( * ) Notice: Subject to any disclaimer, the term of this patent is extended or adjusted under 35 U.S.C. 154(b) by 320 days.

(21) Appl. No.: 17/228,331

(22) Filed: Apr. 12, 2021

(65) Prior Publication Data

US 2021/0358632 A1  Nov. 18, 2021

(30) Foreign Application Priority Data

May 15, 2020 (EP) .................................. 20305500

(51) Int. Cl.
*G16H 50/30* (2018.01)
*G16H 50/20* (2018.01)
(Continued)

(52) U.S. Cl.
CPC ............. *G16H 50/30* (2018.01); *G06F 16/55* (2019.01); *G06F 16/587* (2019.01);
(Continued)

(58) Field of Classification Search
CPC ... G06F 1/00–2221/2153; G16H 10/00–80/00; G06N 3/00–99/007; C12Q 1/00–2300/178
See application file for complete search history.

(56) References Cited

U.S. PATENT DOCUMENTS 10,394,776 B2 * 8/2019 Khan ...................... G16Z 99/00
11,087,888 B2 * 8/2021 Chatterjea .............. G16H 50/80
(Continued)

FOREIGN PATENT DOCUMENTS

WO    WO-2013120199 A1 *  8/2013 ......... G06F 16/2228

OTHER PUBLICATIONS

Kampf et al., "Persistence of coronaviruses on inanimate surfaces and their inactivation with biocidal agents", Journal of Hospital Infection, Elsevier, Amsterdam, NL, vol. 104, No. 3, Feb. 6, 2020, pp. 246-251.

(Continued)

*Primary Examiner* — Jonathon A. Szumny
(74) *Attorney, Agent, or Firm* — Mannava & Kang, P.C.

(57) ABSTRACT

An infection risk prediction system may receive a query associated with an infection risk assessment for a geographic location for an infectious disease and obtain associated infectious disease data. The system detects a plurality of objects at the geographical location and a plurality of material categories for the plurality of objects associated. The system determines a usage frequency indicator and spatial-temporal features for each object and creates a risk prediction model based on the lifespan of the virus on the plurality of material categories for each of the plurality of objects based on the viral disease data and the spatial-temporal features for each object. A risk assessment score for each object is determined and an associated heat map is provided to alert a user of potential virus exposures or to provide a routing application to generate a route that minimizes potential pathogen exposure.

17 Claims, 11 Drawing Sheets

(51) Int. Cl.

| | |
|---|---|
| *G06F 16/75* | (2019.01) |
| *G06F 16/783* | (2019.01) |
| *G06F 16/787* | (2019.01) |
| *G06N 3/08* | (2023.01) |
| *G16H 50/80* | (2018.01) |
| *G06F 16/583* | (2019.01) |
| *G06F 16/587* | (2019.01) |
| *G06F 16/55* | (2019.01) |

(52) U.S. Cl.
CPC .......... *G06F 16/5854* (2019.01); *G06F 16/75* (2019.01); *G06F 16/787* (2019.01); *G06F 16/7837* (2019.01); *G06N 3/08* (2013.01); *G16H 50/20* (2018.01); *G16H 50/80* (2018.01)

(56) References Cited

U.S. PATENT DOCUMENTS

| | | | | |
|---|---|---|---|---|
| 11,529,434 | B1* | 12/2022 | Gurin | A61L 2/24 |
| 2009/0319295 | A1* | 12/2009 | Kass-Hout | G16H 50/80 |
| | | | | 707/999.102 |
| 2016/0171179 | A1* | 6/2016 | Donofrio | G16H 50/80 |
| | | | | 705/2 |
| 2018/0276735 | A1 | 9/2018 | Koenig | |
| 2018/0310890 | A1* | 11/2018 | Li | A61B 5/4842 |
| 2019/0252078 | A1* | 8/2019 | Schubert | G06N 3/044 |
| 2020/0051696 | A1* | 2/2020 | Zhao | G16H 10/60 |
| 2021/0052757 | A1* | 2/2021 | Baarman | G16H 40/20 |
| 2021/0310070 | A1* | 10/2021 | Dillon | G16B 50/30 |

OTHER PUBLICATIONS

Cao Danyang et al., "An improved object detection algorithm based on multi-scaled and deformable convolutional neural networks", Human-centric Computing and Information Sciences, Apr. 11, 2020, 22 pages.

Hang Zhang et al., "Reflectance hashing for material recognition", 2015 IEEE Conference on Computer Vision and Pattern Recognition (CVPR), Jun. 7, 2015, pp. 3071-3080.

Google.com, "COVID-19 Community Mobility Reports", retrieved from the Internet on Apr. 12, 2021, (3 pages). <https://www.google.com/covid19/mobility/>.

Aaple Newsroom, Apple makes mobility data available to aid Covid-19 efforts, Apr. 14, 2020, (4 pages) https://www.apple.com/newsroom/2020/04/apple-makes-mobility-data-available-to-aid-covid-19-efforts/.

European Commission, "ECML Covid", (2020), (1 page) https://jrc-covid.azurewebsites.net/.

Carol Russo, "Israeli Scientists Use AI to detect covid-19 clusters", Nov. 17, 2020, (3 pages), https://www.psychologytoday.com/us/blog/the-future-brain/202003/israeli-scientists-use-ai-detect-covid-19-clusters.

Dr. van Dormalen et al., aerosol and surface stability of Sars cov-2 as compared with Sars Cov-1', Mar. 17, 2020, (5 pages), https://www.nejm.org/doi/full/10.1056/NEJMc2004973C.

Richard Gray, "Covid-19—How long does the coronavirus last on surfaces", Mar. 17, 2020, (5 pages), https://www.bbc.com/future/article/20200317-covid-19-how-long-does-the-coronavirus-last-on-surfaces.

Shigui Ruan, likilihood of survival of corona virus disease 2019, Mar. 30, 2020, (10 pages) https://www.thelancet.com/journals/laninf/article/PIIS1473-3099(20)30257-7/fulltext.

Who, "Coronavirus disease", Oct. 12, 2020, (5 pages) https://www.who.int/news-room/q-a-detail/q-a-coronaviruses.

Webmd, 2005-2021, (4 pages), https://www.webmd.com/lung/how-long-covid-19-lives-on-surfaces.

Accelerate Discovery, "Use deep search to explore the covid-19 corpus", Jan. 5, 2021, (8 pages), https://www.research.ibm.com/covid19/deep-search.

* cited by examiner

INFECTION RISK PREDICTION

CROSS REFERENCE TO RELATED APPLICATIONS

This application is related to and claims priority to European Patent Application Number EP20305500.9 filed on May 15, 2020, the disclosure of which is incorporated by reference in its entirety.

BACKGROUND

Mankind has been struggling with epidemics and infectious diseases since prehistoric times. The infectious diseases caused by various microscopic organisms such as, for example, a virus, a bacteria, a protozoa, and the like have consistently given rise to pandemics. As healthcare facilities across various countries continue to assist the general population assiduously in fighting pandemics and urging the general population to practice home quarantine measures during a pandemic, there has been an increasing concern amongst various sections of society regarding a requirement to be better prepared to handle such pandemics. Specifically, there is a growing concern about protecting oneself during a pandemic and from such experiences in the future.

DETAILED DESCRIPTION

Figure 1:
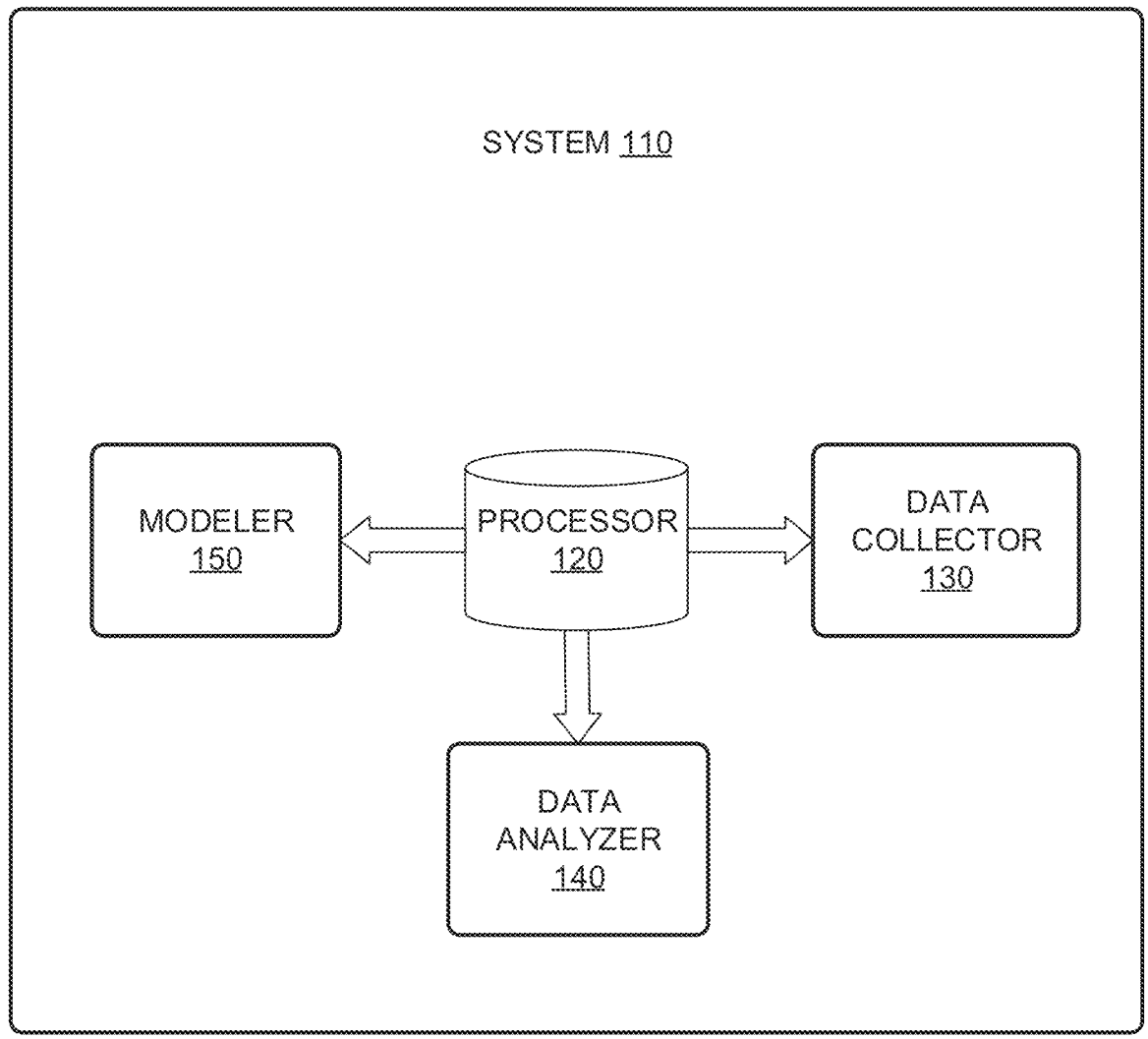
FIG. 1 illustrates an infection risk prediction system, according to an example embodiment of the present disclosure.

For simplicity and illustrative purposes, the present disclosure is described by referring mainly to examples thereof. The examples of the present disclosure described herein may be used together in different combinations. In the following description, details are set forth in order to provide an understanding of the present disclosure. It will be readily apparent, however, that the present disclosure may be practiced without limitation to all these details. Also, throughout the present disclosure, the terms "a" and "an" are intended to denote at least one of a particular element. The terms "a" and "an" may also denote more than one of a particular element. As used herein, the term "includes" means includes but not limited to, the term "including" means including but not limited to. The term "based on" means based at least in part on, the term "based upon" means based at least in part upon, and the term "such as" means such as but not limited to. The term "relevant" means closely connected or appropriate to what is being done or considered.

SUMMARY

The present subject matter relates to infection risk prediction. In an example embodiment, a system including a processor is described. The system includes a data collector coupled to the processor, the data collector to: receive a query associated with a risk assessment for an infectious disease across a geographic location; obtain infectious disease data associated with the infectious disease from a plurality of data sources; detect a plurality of objects associated with the geographical location, the plurality of objects being potentially contaminated with a pathogen associated with the infectious disease; extract spatial-temporal features for each of the plurality of objects, the spatial-temporal features comprising at least one of geospatial data, temporal data, and temperature data associated with each of the plurality of objects; and classify the plurality of objects in a material category from amongst a plurality of material categories, the material category indicative of a surface material associated with each of the plurality of objects. The system also includes a data analyzer coupled to the processor, the data analyzer to determine a usage frequency indicator for each of the plurality of objects based on identification of a plurality of usage parameters associated with each of the plurality of objects; create a material assessment database including details pertaining to a lifespan of the pathogen with respect to each of the plurality of material categories; and create a infection spatial-temporal matrix based on mapping the lifespan of the pathogen corresponding to each of the surface materials for the plurality of objects with the spatial-temporal features for each of the plurality of objects. The system also includes a modeler coupled to the processor, the modeler to: create a risk prediction model associated with each of the plurality of objects based on mapping the infection spatial-temporal matrix with the usage frequency indicator for each of the plurality of objects; determine a risk assessment score for each of the plurality of objects based on implementation of a cognitive learning operation on the risk prediction model associated with each of the plurality of objects, wherein the risk assessment score is indicative of an extent of pathogen exposure associated with each of the plurality of objects; and create a heat map for the geographic location based on the spatial-temporal features for each of the plurality of objects and the risk assessment score for each of the plurality of objects, the heat map being indicative of the extent of the pathogen exposure associated with each of the plurality of objects detected for the geographic location.

In another example embodiment, a method implemented by a processor of a computing system is described. The method includes receiving, by a processor a query associated with a risk assessment for an infectious disease across a geographic location; obtaining, by the processor infectious disease data associated with the infectious disease from a plurality of data sources; detecting, by the processor, a plurality of objects associated with the geographical location, the plurality of objects being potentially contaminated with a pathogen associated with the infectious disease; extracting, by the processor, spatial-temporal features for each of the plurality of objects, the spatial-temporal features comprising at least one of geospatial data, temporal data, and temperature data associated with each of the plurality of objects; classifying, by the processor, the plurality of objects in a material category from amongst a plurality of material categories, the material category indicative of a surface material associated with each of the plurality of objects; determining, by the processor, a usage frequency indicator for each of the plurality of objects based on identification of a plurality of usage parameters associated with each of the plurality of objects; creating, by the processor, a material assessment database including details pertaining to a lifespan of the pathogen with respect to each of the plurality of material categories; creating, by the processor, a infection spatial-temporal matrix based on mapping the lifespan of the pathogen corresponding to each of the surface materials for the plurality of objects with the spatial-temporal features for each of the plurality of objects; creating, by the processor, a risk prediction model associated with each of the plurality of objects based on mapping the infection spatial-temporal matrix with the usage frequency indicator for each of the plurality of objects; determining, by the processor, a risk assessment score for each of the plurality of objects based on implementation of a cognitive learning operation on the risk prediction model associated with each of the plurality of objects, wherein the risk assessment score is indicative of an extent of pathogen exposure associated with each of the plurality of objects; and creating, by the processor, a heat map for the geographic location based on the spatial-temporal features for each of the plurality of objects and the risk assessment score for each of the plurality of objects, the heat map being indicative of the extent of the pathogen exposure associated with each of the plurality of objects detected for the geographic location.

In yet another example embodiment, a non-transitory computer readable medium is described. The non-transitory computer readable medium comprises machine executable instructions that are executable by a processor to: receive a query associated with a risk assessment for an infectious disease across a geographic location; obtain infectious disease data associated with the infectious disease from a plurality of data sources; detect a plurality of objects associated with the geographical location, the plurality of objects being potentially contaminated with a pathogen associated with the infectious disease; extract spatial-temporal features for each of the plurality of objects, the spatial-temporal features comprising at least one of geospatial data, temporal data, and temperature data associated with each of the plurality of objects; classify the plurality of objects in a material category from amongst a plurality of material categories, the material category indicative of a surface material associated with each of the plurality of objects; determine a usage frequency indicator for each of the plurality of objects based on identification of a plurality of usage parameters associated with each of the plurality of objects; create a material assessment database including details pertaining to a lifespan of the pathogen with respect to each of the plurality of material categories; create a infection spatial-temporal matrix based on mapping the lifespan of the pathogen corresponding to each of the surface materials for the plurality of objects with the spatial-temporal features for each of the plurality of objects; create a risk prediction model associated with each of the plurality of objects based on mapping the infection spatial-temporal matrix with the usage frequency indicator for each of the plurality of objects; determine a risk assessment score for each of the plurality of objects based on implementation of a cognitive learning operation on the risk prediction model associated with each of the plurality of objects, wherein the risk assessment score is indicative of an extent of pathogen exposure associated with each of the plurality of objects; and create a heat map for the geographic location based on the spatial-temporal features for each of the plurality of objects and the risk assessment score for each of the plurality of objects, the heat map being indicative of the extent of the pathogen exposure associated with each of the plurality of objects detected for the geographic location.

The present disclosure describes systems and methods for an infection risk prediction including a Infection Risk Prediction System (IRPS). In an example embodiment, the system may include a Coronavirus Risk Assessment Map (CRAMP). The system may determine the extent of potential exposure for a particular pathogen, such as a virus on various objects in the vicinity of a user. In order to mitigate a growing concern about protecting a user during a pandemic or post-pandemic, such as for example, during the current severe acute respiratory syndrome coronavirus 2 ("SARS-CoV-2") pandemic and in the future, the system may provide a demarcation to identify various objects in the vicinity of a user where the user may potentially contract a contagious disease, such as a viral disease. For example, the system may determine and predict an extent of exposure for a particular virus inside a pharmacy, a grocery store, a public bench, a train station, an airport, a vehicle, and the like.

The system may implement various computer vision technologies along with geolocation data to recognize and then identify potentially contaminated surfaces. The system may implement various image-based surface material detection and analysis techniques to determine a surface material associated with the identified risk spots. The system may determine a pathogen's lifespan on the surface material. The system may further determine a frequency of usage of various risk spots by a user. Furthermore, a heat map of various risk spots, where a pathogen may be most likely to survive longer and where a likelihood of a user contracting the pathogen may be higher, such as public benches, metro station accesses, pharmacies, and the like, may be created.

The system may include a processor coupled to a data collector, a data analyzer, and a modeler. The data collector may receive a query associated with an infection risk assessment for a viral disease across a geographic location. The data collector may obtain infection disease data, such as viral disease data associated with a viral disease from a plurality of data sources. The data collector may detect a plurality of objects associated with the geographical location. The plurality of objects may be potentially contaminated with a virus associated with the viral disease. The data collector may extract spatial-temporal features for each of the plurality of objects. The spatial-temporal features may comprise one or more of geospatial data, temporal data, and temperature data associated with each of the plurality of objects. The data collector may classify the plurality of objects in a material category from amongst a plurality of material categories. The material category may indicate a surface material associated with each of the plurality of objects.

The data analyzer may determine a usage frequency indicator for each of the plurality of objects based on the identification of a plurality of usage parameters associated with each of the plurality of objects. The data analyzer may create a material assessment database by populating details pertaining to a lifespan of a virus retrieved from the infection disease data with respect to a surface material for each of the plurality of objects. The data analyzer may create an infection spatial-temporal matrix based on mapping the lifespan of the pathogen corresponding to each surface material for each of the plurality of objects with the spatial-temporal features for each of the plurality of objects.

The modeler may create a infection risk prediction model associated with each of the plurality of objects based on mapping the infection spatial-temporal matrix with the usage frequency indicator for each of the plurality of objects. The modeler may determine a risk assessment score for each of the plurality of objects based on the implementation of a cognitive learning operation on the infection risk prediction model associated with each of the plurality of objects. The risk assessment score may be indicative of the extent of pathogen exposure or infection exposure associated with each of the plurality of objects. The modeler may create a heat map for the geographic location based on the spatial-temporal features for each of the plurality of objects and the risk assessment score for each of the plurality of objects. The heat map may be indicative of the extent of the pathogen exposure associated with each of the plurality of objects detected for the geographic location. Accordingly, using the heat map, a user may easily identify probable contaminated surfaces and/or objects to avoid getting infected and spreading the associated disease further.

FIG. 1 illustrates a system 110 for infection risk prediction (referred to as system 110 hereinafter), according to an example implementation of the present disclosure. For the sake brevity and ease of explanation, the present disclosure is explained in detail with respect to a viral infection; however, it will be appreciated that the concepts described herein may be extended to systems for determining risk prediction by other pathogen agents, such as bacteria, a protozoa, and the like.

In an example, the system 110 may include a processor 120. The processor 120 may be coupled to a data collector 130, a data analyzer 140, and a modeler 150.

The data collector 130 may receive a query associated with a virus risk assessment for a viral disease across a geographic location. In an example embodiment, the viral disease associated with the query is a severe acute respiratory syndrome coronavirus 2 ("SARS-CoV-2"). One of ordinary skill in the art will appreciate that in the alternative embodiments a viral disease may include any disease that may be caused by pathogenic agents. The geographic location may be an environment in the vicinity of a user. For example, the geographic location may be a location such as a pharmacy, a grocery store, a public bench, a train station, an airport, a vehicle, and the like. The geographic location may be part of a route that a user may wish to follow to reach a destination.

The data collector 130 may obtain infection disease data, interchangeably referred to as viral disease data associated with the viral disease from a plurality of data sources. The plurality of data sources may include various databases maintained by various organizations across the world. The infection disease data may include various details pertaining to pathogen like a virus, such as the life cycle of a virus on various types of surfaces, materials, and the like. The viral disease data may also include statistics related to survival and sustenance of the virus in various environments, geological conditions, temperature conditions, pH conditions, and the like. The viral disease data may also include mobility data associated with the virus. In addition, the viral disease data may include results from various data monitoring initiatives and national policies associated with the virus. The viral disease data may also include viral cluster prediction data such as data related to the spreading of the virus in various geographical clusters. The viral disease data may also include survival data for a virus. Furthermore, the viral disease data may include information on infections caused by a virus. In an example embodiment, the viral disease data may include specified research such as for example, artificial intelligence-based research service around SARS-CoV-2, studies on surfaces for SARS-CoV-2, and the like. One of ordinary skill in the art will appreciate that the viral disease data may include any other type of data associated with a virus.

The data collector 130 may detect a plurality of objects associated with the geographical location. The plurality of objects may be potentially contaminated with a virus associated with the viral disease. The plurality of objects may include various vehicles in the vicinity of a user, a signboard, a platform for keeping various objects, a public bench, a public drinking water facility, various items and access areas in and around various locations such as a grocery store, a pharmacy, a train access, and the like (an exemplary image for the plurality of objects illustrated by way of FIG. 5). The data collector 130 may detect the plurality of objects from an image, a video-based medium, a uniform resource locator (URL), a geolocation, and a data stream associated with the geographic location. For the purpose of this document, the image, the video-based medium, the URL, the geolocation, and the data stream associated with the geographic location may be collectively referred to by using the term "media". The data collector 130 may extract a plurality of image frames from the media (described in detail with respect to description of FIG. 2).

The data collector 130 may extract spatial-temporal features for each of the plurality of objects. The spatial-temporal features may comprise geospatial data, temporal data, and temperature data associated with each of the plurality of objects. The spatial-temporal features may describe a phenomenon in a certain location and time. The spatial-temporal features of the plurality of objects may include one or more spatial features of each of the plurality of objects and one or more temporal features of each of the plurality of objects. The data collector 130 may extract the spatial-temporal features for each of the plurality of objects based on neural network-based feature extraction layers implemented on the plurality of image frames. The neural network-based feature extraction layers may implement a semantic segmentation on the plurality of image frames to extract the spatial-temporal features. The data collector 130 may receive the media comprising the plurality of image frames.

The data collector 130 may classify the plurality of objects in a material category from amongst a plurality of material categories. Each of the plurality of material categories may comprise a surface material associated with each of the plurality of objects. The plurality of material categories may be, for example, a metal, an alloy, a plastic, a cloth, a canvas, a rubber, a glass, wood, water, soil, and the like. The surface material may be a material on a surface of an object such as metal may be the surface material for a car, the cloth may be the surface material for a human being, and the like.

The data collector 130 may determine the plurality of material categories based on an analysis of a reflectance attribute associated with the surface material associated with each of the plurality of objects. The reflectance attribute may refer to a measure of light or other radiation that may be striking a surface and is reflected off it. The data collector 130 may determine the plurality of material categories based on an analysis of a plurality of material attributes associated with the surface material associated with each of the plurality of objects. The data collector 130 may identify the plurality of objects based on a semantic segmentation technique.

The data analyzer 140 may determine a usage frequency indicator for each of the plurality of objects based on the identification of a plurality of usage parameters associated with each of the plurality of objects. The plurality of usage parameters may be measurable factors for the object to be evaluated. For example, the plurality of usage parameters may include a user touch propensity, a user accessibility, a user interest in interaction, and the like. The plurality of usage parameters may classify the objects as a "high user touch propensity" and as a "low user touch propensity". For example, if an object may be positioned where several people can touch it or interact with it, then the object may be determined to be high user touch propensity. Additionally, if an object is on a table it might be more accessible than an object on a shelf, and hence may be classified as having a high user touch propensity. Furthermore, a natural object such as a stream of water, a boulder, and the like may be less likely to be touched by a user and hence may be classified by the data analyzer 140 as having low user touch propensity.

The data analyzer 140 may create a material assessment database by mapping the lifecycle of a virus retrieved from the viral disease data with the surface material for each of the plurality of objects. The material assessment database may comprise a lifespan of the virus corresponding to each of the surface materials.

The data analyzer 140 may create a virus spatial-temporal matrix based on mapping the lifespan of the virus corresponding to each of the surface material for each of the plurality of objects with the spatial-temporal features for each of the plurality of objects. For example, the data analyzer 140 may map the lifespan of a virus on a glass surface in a cold temperature environment, during a time period of, for example, 6 AM-12 Noon to create the virus spatial-temporal matrix.

The modeler 150 may create a viral risk prediction model associated with each of the plurality of objects based on mapping the virus spatial-temporal matrix with the usage frequency indicator for each of the plurality of objects. After the data analyzer 140 has determined the virus spatial-temporal matrix for each object, and the usage frequency indicator for each object, the modeler 150 may map the usage frequency indicator with the virus spatial-temporal matrix to create the viral risk prediction model. The viral risk prediction model may include a prediction for contracting a virus when coming in contact with a particular object The modeler 150 may determine a risk assessment score for each of the plurality of objects based on the implementation of a cognitive learning operation on the viral risk prediction model associated with each of the plurality of objects. The risk assessment score may be indicative of the extent of virus exposure associated with each of the plurality of objects as explained in detail with respect to description of FIG. 2.

Figure 8:
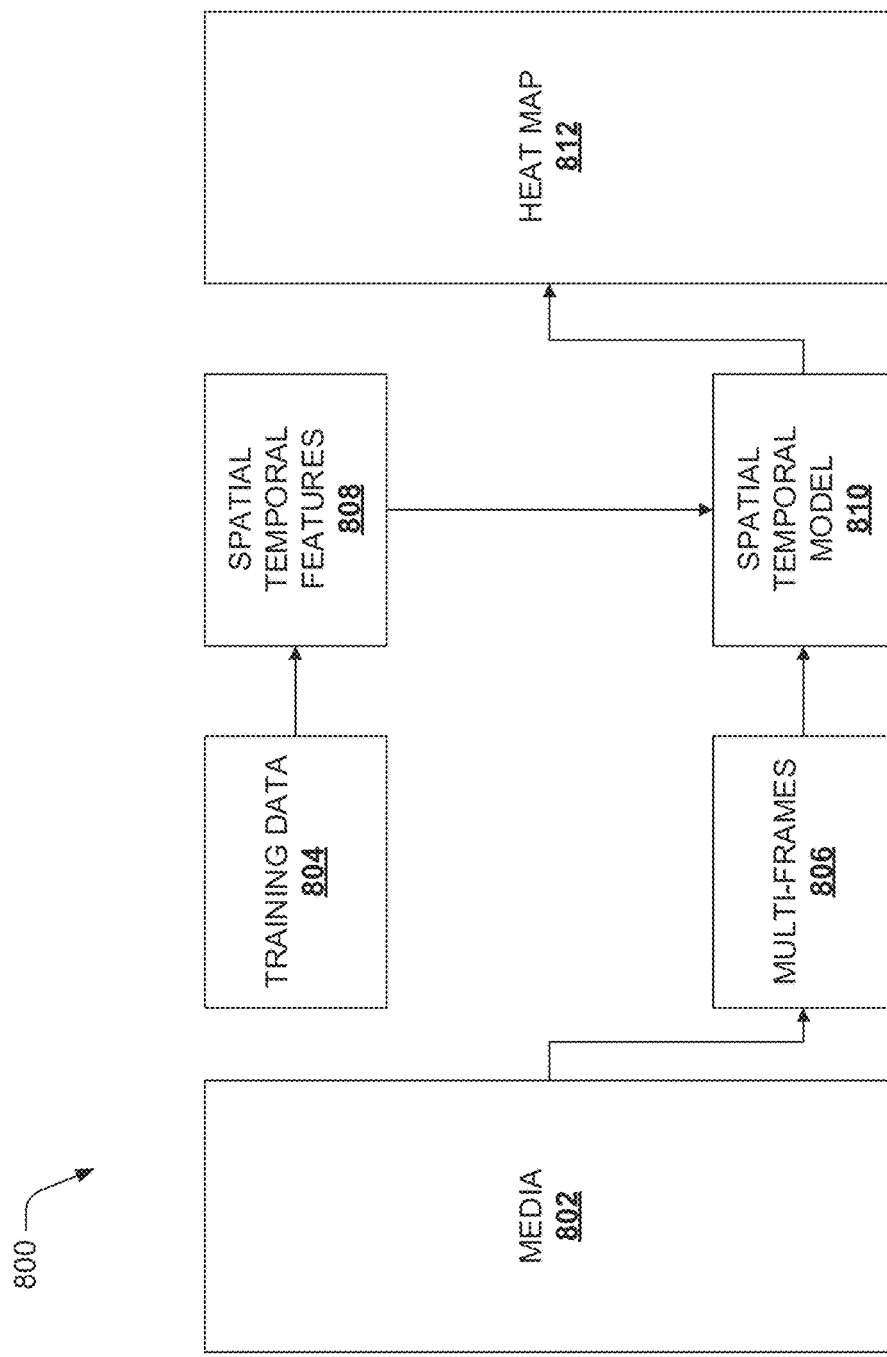
FIG. 8 illustrates heat map generation for the infection risk prediction using the infection risk prediction system, according to an example embodiment of the present disclosure.

Based on the spatial-temporal features for each of the plurality of objects and the risk assessment score for each of the plurality of objects, the modeler 150 may create a heat map of the geographic location (described in detail with respect to description of FIG. 8). The heat map may be indicative of the extent of the virus exposure associated with each of the plurality of objects detected for the geographic location. For an object, from among the plurality of objects, having the risk assessment score above a threshold risk assessment score, a cleaning alert for a user may be generated by the modeler 150. The threshold risk assessment score may be pre-defined by an authorized personnel or may be dynamically configurable. In an example embodiment, the threshold risk assessment score may be determined using data that may be collected by the data collector 130 and analyzed by the data analyzer 140, such as survival rate or time of a virus on different surfaces, known mobility reports for the virus, local weather information and the like. Further, the system 110 may include a pre-configured recommendation scale that may facilitate the determination of a threshold limit for the risk assessment score based on the virus spatial-temporal matrix and the viral disease data. Thus, a score greater than the threshold score may indicate a likelihood of exposure to the pathogen with a risk of catching the infection, while a score lower than the threshold score may indicate no or minimal risk of catching the infection.

Figure 2:
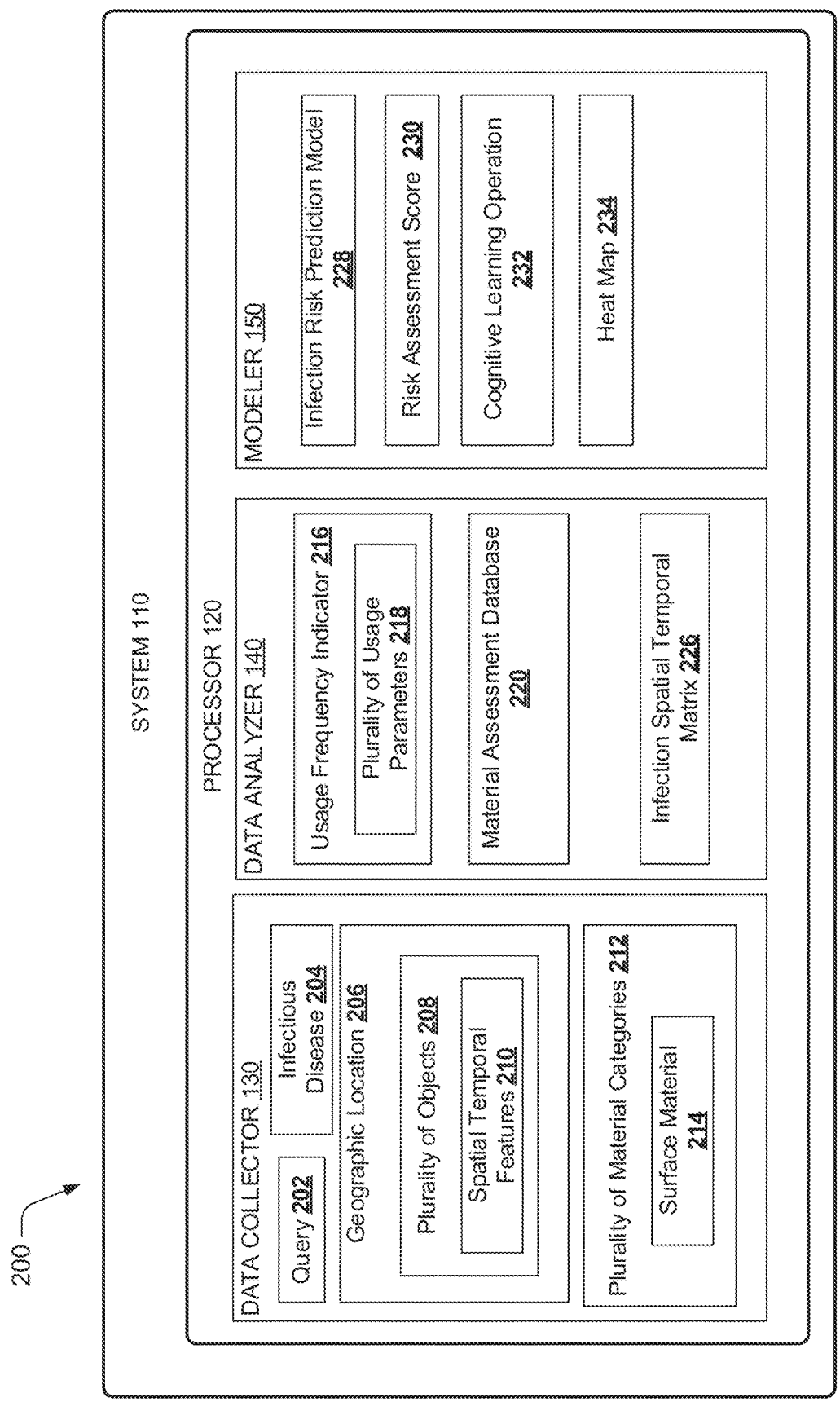
FIG. 2 illustrates various components of the infection risk prediction system, according to an example embodiment of the present disclosure.

FIG. 2 illustrates various components of the system 110, according to an example embodiment of the present disclosure. As illustrated, the system 110 may include the processor 120 coupled to the data collector 130, the data analyzer 140, and the modeler 150.

The data collector 130 may receive a query 202 associated with a virus risk assessment for a viral disease 204 across a geographic location 206. In an example embodiment, the viral disease 204 associated with the query 202 is SARS-CoV-2. One of ordinary skill in the art will appreciate that in alternative embodiments the viral disease 204 may include any disease that may be caused by other pathogenic agents. The geographic location 206 may be an environment in the vicinity of a user. For example, the geographic location 206 may be a location, such as a pharmacy, a grocery store, a public bench, a train station, an airport, a vehicle, and the like. The geographic location 206 may be part of a route that a user may wish to follow to reach a destination.

The data collector 130 may obtain viral disease data associated with the viral disease 204 from a plurality of data sources. As discussed above, the viral disease data may include various details pertaining to a virus, such as a lifespan of the virus on various surfaces, and survival and sustenance rate of the virus in various environments.

The data sources may include various databases maintained by various organizations across the world. The data sources may include databases such as Google community mobility report®, Apple mobility data®, European Crisis Management Laboratory®, New England Journal of Medicine®, The Lancet Infectious Diseases®, World Health Organization® Questions and Answers, WebMD®, IBM Deep search®, Wikipedia®, Coronaisrael, and the like. The system 110 may provide access to a user for allowing entry of any update in the viral disease data for a particular geographical location. In an example, the system 110 may be configured to automatically retrieve relevant viral disease data from the data sources. In another example, the system 110 may require manual intervention for retrieving relevant viral details from some of the data sources.

The data collector 130 may detect a plurality of objects 208 associated with the geographical location. The objects 208 may be potentially contaminated with a pathogenic agent such as a virus associated with the viral disease 204. The objects 208 may include various vehicles in the vicinity of a user, a signboard, a platform for keeping various objects, a public bench, a public drinking water facility, various items and access areas in and around various public places such as a grocery store, a pharmacy, a train access, and the like (an exemplary image for the objects 208 illustrated by way of FIG. 5). The data collector 130 may detect the objects 208 from an object identification media providing details pertaining to the objects. Examples of the object identification media include, but are not limited to, an image, a video-based medium, a uniform resource locator, a geolocation, and a data stream associated with the geographic location 206.

To detect the objects 208, the data collector 130 may extract a plurality of image frames from the media of the geographic location where the objects 208 are located. In an example, the data collector 130 may implement computer vision-based object detection techniques for detecting the objects 208 associated with the geographical location from the object identifying media. In an example embodiment, the computer vision-based object detection techniques may include a You Only Look Once (YOLO) object detection technique. YOLO is a computer vision object detection technique that may enable the processing of an image straight from image pixels to bounding box coordinates and class probabilities.

The object detection technique deployed by the system 110 may extract various image pixels for the object identifying media. The object detection technique may analyze the pixels and extract various features of a pixel. The technique may define bounding boxes for defining coordinates of various objects (illustrated by FIG. 5). The image pixels and the bounding boxes may be analyzed to predict objects within a bounding box. The bounding box may be an image boundary within which an object may be present in an image. For example, an input image may be classified into an "X" bounding boxes (x, y, w, h). The (x, y) coordinates may represent edges of the box relative to the input image and width (w) and height (h) may be predicted relative to the input image. The technique may analyze all the pixels from each bounding box and join features for all pixels therein to predict object(s) present in each bounding box. In an example, the bounding boxes for multiple objects may overlap such as a motorbike and a bike rider may overlap over the same coordinates (x, y). The data collector may detect multiple objects for the same bounding box. One of ordinary skill in the art will appreciate that any other computer vision-based object detection technique may also be trained and implemented to extract and analyze the image pixels and to predict and analyze the bounding boxes.

The data collector 130 may extract spatial-temporal features 210 for each of the objects 208. The spatial-temporal features 210 may comprise geospatial data, temporal data, and temperature data associated with each of the objects 208. The spatial-temporal features 210 may describe a particular phenomenon in a certain location and time. The spatial-temporal features 210 of the objects 208 may include one or more spatial features of each of the objects 208 and one or more temporal features of each of the objects 208. In an example, the one or more spatial features of each of the objects 208 may include one or more of color features, texture features, shape features, and size features. Furthermore, the one or more temporal features of the objects 208 include one or more of motion features, trajectory features, time of a day identifying features, and flicker features.

The data collector 130 may extract the spatial-temporal features 210 for each of the objects 208 based on neural network-based feature extraction layers implemented on the plurality of image frames. The neural network-based feature extraction layers may implement a semantic segmentation on the plurality of image frames to extract the spatial-temporal features 210. The data collector 130 may receive the media comprising the plurality of image frames.

The data collector 130 may segment the image frames into multiple media objects based on semantically meaningful parts of the media such as vehicles, people, trolleys, consumables, and the like. Subsequently, the data collector 130 may select one or more media objects from amongst the media objects based on pre-defined conditions. In an example embodiment, the pre-defined conditions may include conditions that may be related to an area and shape of the media objects. For example, for a pharmacy, the pre-defined conditions may be the detection of consumables, and for a train station, the pre-defined conditions may include detection of various people, train surfaces, screens, and the like. The temperature data may include average temperature predicted for the geographic location 206. Based on various factors mentioned above, the objects 208 may be identified from the media. For example, the objects 208 may include a shelf in a grocery store, a medicine counter, a car, a bicycle, and the like.

The data collector 130 may classify the objects 208 in a material category from amongst a plurality of material categories 212. Each of the material categories 212 may comprise a surface material 214 associated with each of the objects 208. The material categories 212 may be, for example, a metal, an alloy, a plastic, a cloth, a canvas, a rubber, a glass, wood, water, soil, and the like. The surface material 214 may be a material on a surface of an object such as metal may be the surface material 214 for a car, the cloth may be the surface material 214 for a human being, and the like.

The data collector 130 may determine the material categories 212 based on an analysis of a reflectance attribute associated with the surface material 214 associated with each of the objects 208. The reflectance attribute may refer to a measure of light or other radiation that may strike a surface and is reflected off it. The data collector 130 may determine the material categories 212 based on an analysis of a plurality of material attributes associated with the surface material 214 associated with each of the objects 208. The plurality of material attributes may refer to various physical qualities of a material such as a color, a texture, a shape, and the like.

The data collector 130 may identify the objects 208 based on the semantic segmentation technique. The semantic segmentation may be implemented on the image pixels extracted from the image frames as mentioned above. The data collector 130 may identify the surface material 214 based on the semantic testing of the objects 208. The data collector 130 may implement various image pixel classification based techniques for material detection other than those mentioned herein. The data collector 130 may implement the image-based material detection so that there may be no overlap amongst various materials detected for an image pixel, unlike object detection wherein an overlap may be detected. The material detection may detect the surface material 214 in a continuous manner with no overlapping surface materials. Such techniques may improve the accuracy of the detection and may also enhance the efficiency of the system 110 in performing virus risk prediction. For example, if an object is a car, then the surface material 214 may be determined as a combination of metal, glass, and plastic. If an object is a table, then the surface material 214 may be determined as one of a metal, a wood piece, a polymer, and the like. The data collector 130 may further implement image-based reflectance testing and image-based material detection to identify the reflectance attribute and the material attributes to identify the material category. For example, the data collector 130 may identify the position of the surface material 214 such as the metal, the glass, and the plastic over an image of a car based on image-based reflectance detection. The data collector 130 may create a database for storing the reflectance attributes and the plurality of material attributes associated with each of the objects 208.

The data analyzer 140 may determine a usage frequency indicator 216 for each of the objects 208 based on the identification of a plurality of usage parameters 218 associated with each of the objects 208. The plurality of usage parameters 218 may be measurable factors for the object to be evaluated. For example, the plurality of usage parameters 218 may include a user touch propensity, a user accessibility, a user interest in interaction, and the like. The plurality of usage parameters 218 may classify the objects as a "high user touch propensity" and as a "low user touch propensity". For example, if an object may be positioned where several people can touch it or interact with it, then the object may be determined to be high user touch propensity. Additionally, if an object is on a table it might be more accessible than an object on a shelf, and hence may be determined to have a higher user touch propensity. Further, a natural object such as a boulder, mountain cliff, treetop, and the like may be less likely to be touched by a user and hence may be classified by the data analyzer 140 as having a low user touch propensity.

According to an example, objects may be captured in media such as, for example, a wall, a building, a house, a window, a door, a table, a painting, a bulletin board, a poster, a TV, a screen, a table, a bus, a car, an airplane, sky, a tree, grass, flowers, rocks, sand, a boulder, mountains, hill, a stream, and a river. Then the wall, the house, the window, the door, the painting, the bulletin board, the table, the poster, the TV, the screen, the table, the bus, and the car may be considered as high user touch propensity. On the other hand, one or more of the natural objects, such as one or more of the sky, the tree, the grass, the flowers, the rocks, the sand, the boulder, the mountains, the airplane, the hill, the building, the stream, and the river may be considered low user touch propensity. Similarly, the data analyzer 140 may determine the usage frequency indicator 216 for each of the objects 208 detected across the geographic location 206.

The data analyzer 140 determines a unique usage frequency indicator 216 for a user based on the identification of the plurality of usage parameters 218 unique to the user. For example, the data analyzer 140 may require input from each user about how frequently they are in direct interaction with an object, such as for example, a book, a car, a screen, and the like. If for example, a user may never touch books they may be given a low user touch propensity for books every time a book may be detected as an object for the user. If for example, a user may always touch the screen they may be given a high user touch propensity for screens every time a screen may be detected as an object for the user.

The data analyzer 140 may create a material assessment database 220 by mapping the lifecycle of a virus retrieved from the viral disease data with the surface material 214 for each of the objects 208. The material assessment database 220 may comprise of a lifespan of the virus corresponding to each of the surface material 214. The data analyzer 140 may retrieve lifecycle data for a virus on various surfaces and map the same with the surface material 214 identified for the objects 208. For example, the data analyzer 140 may retrieve the lifespan of the virus on a glass surface, a metal surface, a wooden surface and the like to create the material assessment database 220.

The data analyzer 140 may create an infection spatial-temporal matrix 226, also referred to as, virus spatial-temporal matrix 226 based on mapping the lifespan of the virus corresponding to each of the surface material 214 for each of the objects 208 with the spatial-temporal features 210 for each of the objects 208. For example, the data analyzer 140 may map the lifespan of the virus on a glass surface in a cold temperature environment, during a time period of, for example, 6 AM-12 Noon. As mentioned above, the spatial-temporal features 210 may include geospatial data. The data analyzer 140 may retrieve geospatial data such as the spread of a virus in a particular geographic location 206 such as, a country and use the same to create the virus spatial-temporal matrix 226 for a location in that country. Therefore, the data analyzer 140 may create the virus spatial-temporal matrix 226 for each of the objects 208 by considering the virus lifespan on the surface material 214 for that object, the geospatial data for the geographic location 206 associated with the object, and the temperature of the environment associated with that object. The temperature of the environment may affect various viruses, which may not be able to survive above or below a certain temperature. In an example embodiment, the data analyzer 140 may create the virus spatial-temporal matrix 226 for each object by considering the virus lifespan on the surface material 214 for that object, the geospatial data for the geographic location 206 associated with the object, the temperature of the environment associated with that object, and a distance between that object and a user of the system. In an example, the data analyzer 140 may determine the distance between that object and a user of the system by implementing an image-based depth calculation.

The modeler 150 may create an infection risk prediction model also referred to as a viral risk prediction model 228 associated with each of the objects 208 based on mapping the virus spatial-temporal matrix 226 with the usage frequency indicator 216 for each of the objects 208. After the data analyzer 140 has determined the virus spatial-temporal matrix 226 for each object, and the usage frequency indicator 216 for each object, the modeler 150 may map the usage frequency indicator 216 with the virus spatial-temporal matrix 226 to create the infection risk prediction model, interchangeably referred to as the viral risk prediction model 228. The viral risk prediction model 228 may include a prediction for contracting a virus when a user may come in contact with a particular object. For example, the virus spatial-temporal matrix 226 may be created for a wooden table in a grocery store of a country with an epidemic occurrence recent past. The usage frequency indicator 216 for the table may be determined as a high user touch propensity (as mentioned above). The modeler 150 may map the virus spatial-temporal matrix 226 and the usage frequency indicator 216 for the wooden table and present the viral risk prediction model 228 associated with the wooden table in a grocery store of a country with an epidemic occurrence in recent past to a user of the system 110.

The modeler 150 may determine a risk assessment score 230 for each of the objects 208 based on the implementation of a cognitive learning operation 232 on the viral risk prediction model 228 associated with each of the plurality of objects 208. The risk assessment score 230 may be indicative of the extent of contracting the virus on exposure to each of the objects 208. In an example embodiment, the risk assessment score 230 may be calculated based on the following equation:

$$Risk_{Virus\ \alpha, X, Y} = \sum_{i=1}^{m}(Obj_{i,X,Y} * F_{Obj\ i}) * LS_{Virus\ \alpha}(Mat_{X,Y})$$

In an alternative embodiment, the risk assessment score 230 may be calculated based on the following equation:

$$Risk_{Virus\ \alpha, X, Y} = MAX_{i=1}^{m}(Obj_{i,X,Y} * F_{Obj\ i}) * LS_{Virus\ \alpha}(Mat_{X,Y})$$

Where,
Virus $\alpha$=The virus selected by a user associated with the viral disease 204,
M=Number of objects detected for a geographic location 206,
X, Y=Coordinates for the geographic location 206 associated with the query 202,
$Obj_{X,Y}$="1", if the object detected may be present in the coordinates X, Y and "0" of the object detected may not be present in the coordinates X, Y,
$F_{Obj\ i}$=The frequency of use of the object (the usage frequency indicator 216 mentioned above), the value may range from 0-1, wherein 0 may be low frequency and 1 may be high frequency. Alternatively, 0 may be a low user touch propensity indicator, and 1 may be a high user touch propensity indicator.
$Mat_{X,Y}$=The surface material 214 detected for the object present in the coordinates X, Y,
$LS_{Virus\ \alpha}$=Coefficient of risk of virus presence based on the lifespan of the virus on the material. The value may be from zero-one (0-1), wherein zero (0) may denote a low chance of survival and one (1) may denote a high chance of survival. This value may be determined by the virus spatial-temporal matrix 226. For example, the virus spatial-temporal matrix 226 may indicate that a virus may be able to sustain itself on a metal surface for a duration of twelve (12) hours and the same virus may be able to sustain itself on a wooden surface for a duration of 10 minutes. The modeler 150 may determine the value of $LS_{Virus\ \alpha}$ to be closer to zero (0) for the wooden surface and the value of $LS_{Virus\ \alpha}$ to be closer to one (1) for the metal surface.

In an example embodiment, the aforementioned calculations may be performed at the pixel level of an image for each object. In an example embodiment, the risk assessment score may be calculated at a pixel level, wherein the modeler 150 may analyze the objects 208 pixel by pixel. As mentioned above, the data collector may identify multiple objects on one pixel. The modeler may analyze all the objects present on the same pixel and multiply the result with the usage frequency indicator 216 for each of those objects present on that same pixel. For example, if a pixel may include a motorbike and a bike rider, the modeler 150 may consider both the motorbike and the bike rider for calculation of the risk assessment score 230. The modeler 150 may implement the equation presented above for both the motorbike and the bike rider and determine the risk assessment score 230 therefrom. The $MAX_{i=1}^{m}$ mentioned above may determine the risk assessment score 230 for multiple objects in the same pixel based on a maximum risk value amongst those objects detected in the same pixel.

In an example embodiment, the modeler 150 may deploy various machine learning techniques such as for example, a learning loop-based technique that may adjust the equations mentioned above for determining the risk assessment score 230 based on feedback from a user. The modeler 150 may include various other coefficients in the aforementioned calculations other than those mentioned above for the determination of the risk assessment score 230. In an example embodiment, these calculations are performed at the pixel level of an image for each object. One of ordinary skill in the art will appreciate that the calculations described above are examples only. Other techniques may be used for calculating a risk assessment score without departing from the scope of the disclosure. For example, coefficients other than those pertaining to a lifespan of the virus on a material may be used to calculate the risk assessment score 230.

Based on the spatial-temporal features 210 for each of the objects 208 and the risk assessment score 230 for each of the objects 208, the modeler 150 may create a heat map 234 for the geographic location 206 (described in detail with respect to description of FIG. 8). The heat map 234 may be indicative of the extent of the virus exposure associated with each of the objects 208 detected for the geographic location 206. In an example embodiment, the modeler 150 may implement Convolution Neural Network (CNN) model, such as a spatial-temporal CNN model, to create the heat map 234. The CNN model may be pre-trained based on a training dataset. The training dataset may include, but not limited to, training images, the objects 208 detected from the training images, the surface material detection for the training images, and spatial-temporal features 210 of the training images. It can be appreciated that the heat map may be rendered in two or three dimensions as may be appropriate for user consumption. For example, an overhead two-dimensional representation may be appropriate for a route planning application, while a three-dimensional representation may be useful in an augmented reality application.

For an object, from among the objects 208, having the risk assessment score 230 above a threshold risk assessment score, a cleaning alert for a user may be generated by the modeler 150. In an example, a user of the system may provide a value for the threshold risk assessment score. The cleaning alert may be used to generate a recommendation for a cleaner to clean a surface of the object if the risk assessment score 230 may be above the threshold risk assessment score. The cleaning alert may facilitate the cleaning of areas with the highest contamination on priority. For example, the cleaning alert may indicate that the wooden table in a grocery store may be cleaned on a priority basis, because it may be an object with a high risk assessment score 230.

In an example embodiment, the heat map 234 may be displayed to a user or provided as an input to an application for further analysis regarding risk assessment. For example, the heat map 234 may be provided as a visualization that is overlaid on a live camera view on a display of the user's mobile device. In another example embodiment, the heat map 234 may be provided as an input to a routing application on the user's mobile device. Based on the heat map 234, a route, from a plurality of routes, may be recommended to the user. The recommended route may minimize potential virus exposure and/or may have the least likely virus exposure potential as explained in detail in the following paragraphs.

In an example embodiment, a cumulative risk assessment score for each location spot on a route may be determined. The cumulative risk assessment score for a location spot may be determined based on a cumulative total of the risk assessment score 230 for the objects 208 in the location spot on the route. Furthermore, it may be ascertained whether the cumulative risk assessment score may be above a pre-defined limit for the location spot to assess the risk associated with the corresponding location spot. The pre-defined limit for the location spot may be determined by analyzing data collected by the data collector 130, such as survival and sustenance rate of a virus on various surfaces, known mobility reports for the virus, local weather information, and the like. In an example embodiment, the pre-defined limit may be determined by authorized personnel and/or may be dynamically configurable.

The heat map 234 may include the cumulative risk assessment score corresponding to each location spot on the route. In an example embodiment, the routing application may collect details pertaining to the location spots, where the cumulative risk assessment score may be above the pre-defined limit over a route starting from a departure spot to an arrival spot. The routing application may identify one or more location spots with the cumulative risk assessment score above the pre-defined limit on the heat map 234, for example, similar to a traffic congestion situation, and may present alternate routes to a user. Further, a route risk assessment score for the route may be determined by adding the cumulative risk assessment score for each location spot on that route from the departure spot to the arrival spot. The routing application may determine a route amongst the plurality of routes with a lowest value of the route risk assessment score. Accordingly, a route that minimizes virus exposure potential based on the route risk assessment score may be recommended to a user.

Figure 3:
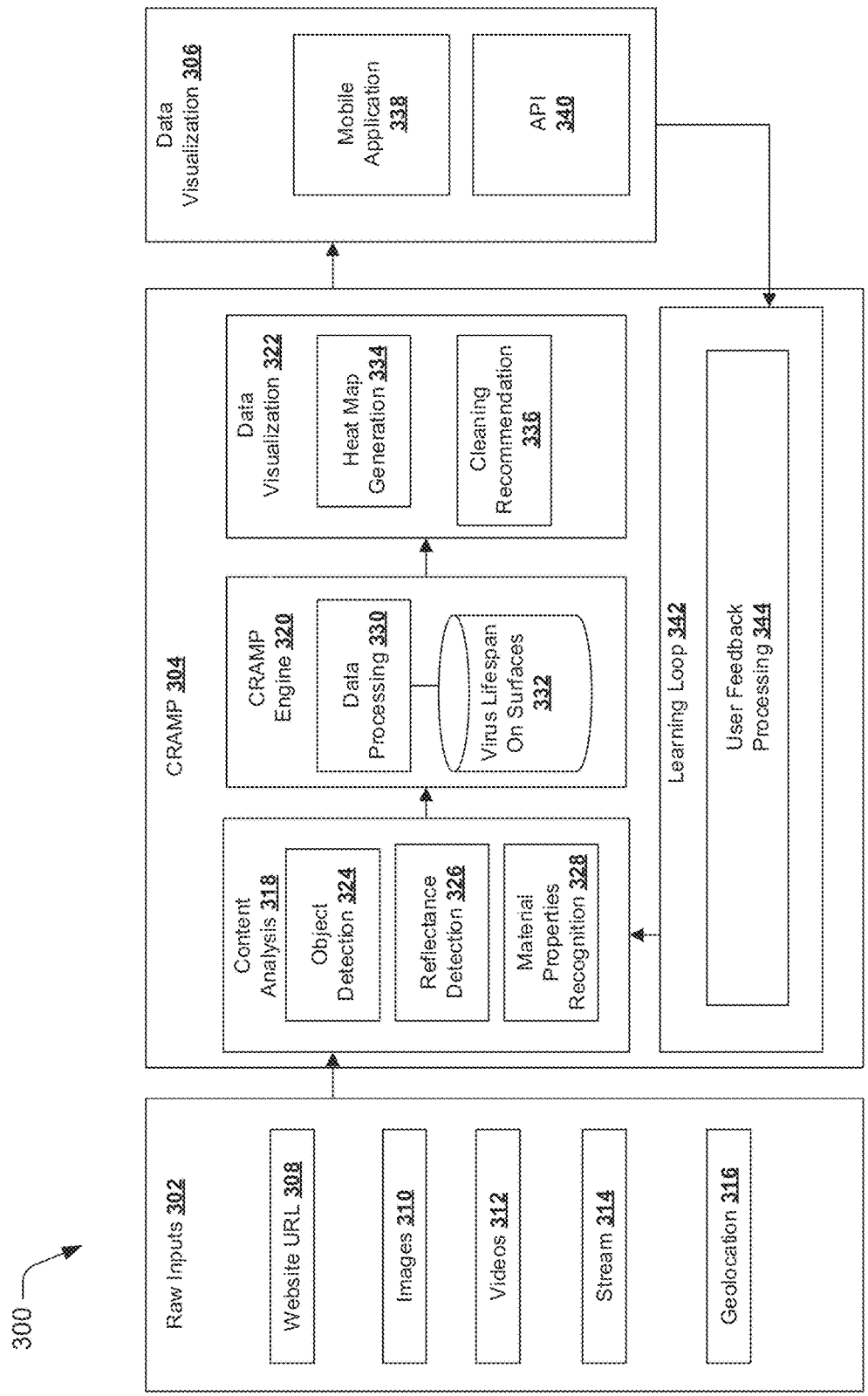
FIG. 3 illustrates an architectural flow diagram for infection risk prediction using the infection risk prediction system, according to an example embodiment of the present disclosure.

FIG. 3 illustrates an architectural flow diagram 300 for infection risk prediction using the system 110, according to an example embodiment of the present disclosure. Any of the components described above may be referred to hereinafter. For the purpose of explanation, and not as a limitation, the flow diagram 300 illustrates a workflow diagram for the CRAMP mentioned above as an exemplary embodiment of the present disclosure. The flow diagram 300 may include a raw input component 302, a CRAMP processor 304, and a data visualization 306. The raw input component 302 may include a website URL 308, an image set 310, a video set 312, a data stream 314, and a geolocation 316. The website URL 308, the image set 310, the video set 312, the data stream 314, and the geolocation 316 have been described above as the media.

The raw input component 302 may provide input to the CRAMP engine 304. The CRAMP processor 304 may include a content analysis component 318, a CRAMP engine 320, and a data visualization component 322. The content analysis component 318 may further include an object detection 324 (described in detail with respect to description of FIG. 2).The content analysis component 318 may further include a reflectance detection 326 (described in detail with respect to description of FIG. 2). The content analysis component 318 may further include a material property recognition 328 (described in detail with respect to description of FIG. 2). The CRAMP engine 320 may include a data processing component 330 and a virus lifespan on surface database 332, also referred to as database 332. The database 332 may include the virus spatial-temporal matrix 226. The data processing component 330 may determine the usage frequency indicator 216 and create the material assessment database 220 mentioned above. The data visualization component 322 may include a heat map generation 334 and a cleaning recommendation 336. The heat map generation 334 may include the creation of the heat map 234. The cleaning recommendation 336 may be the cleaning alert described by way of FIG. 1 and FIG. 2. The CRAMP processor 304 may further include a learning loop 342. The learning loop 342 may include a user feedback processing component 344.

The CRAMP processor 304 may provide an output to a user through the data visualization 306. The data visualization 306 may include a mobile application 338 and an application programming interface (API) 340. The mobile application 338 and the API 340 may be used by a user to interact with the system 110. The data visualization 306 may be used by the user to provide a user feedback to the system 110. As mentioned above, the modeler 150 may determine the risk assessment score 230 for each of the objects 208 based on the implementation of the cognitive learning operation 232 on the viral risk prediction model 228 associated with each of the objects 208. The data visualization 306 may facilitate a learning loop function of the cognitive learning operation 232 by providing the user feedback to the CRAMP processor 304. The CRAMP processor 304 may process the user feedback using the user feedback processing component 344 and provide input to the learning loop 342. The learning loop 342 may update the cognitive learning operation 232 based on the user feedback.

The CRAMP processor 304 may process the user feedback using the user feedback processing component 344 and provide input to the learning loop 342. The learning loop 342 may update the cognitive learning operation 232 based on the user feedback to determine a unique usage frequency indicator 216 for a user.

Figure 4:
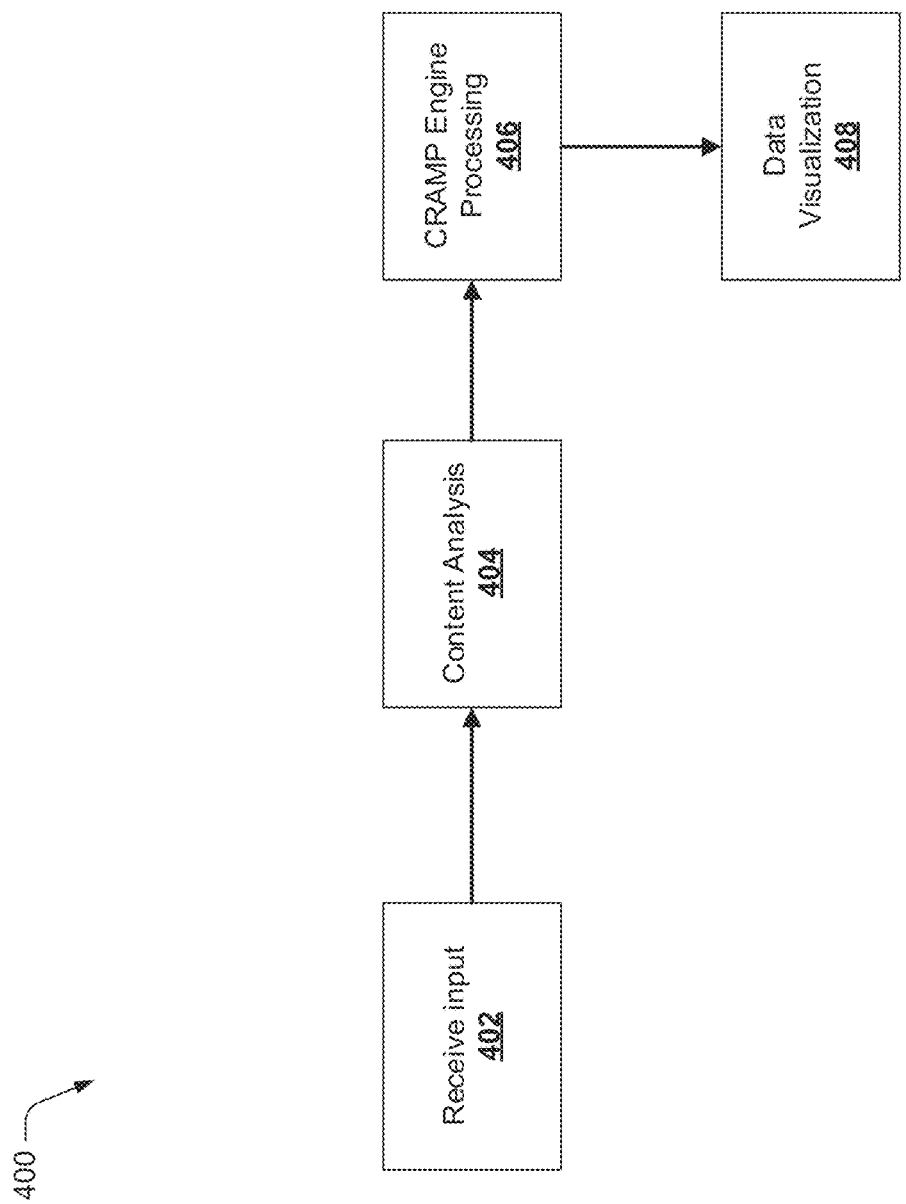
FIG. 4 illustrates a workflow diagram for the infection risk prediction using the infection risk prediction system, according to an example embodiment of the present disclosure.

FIG. 4 illustrates a workflow diagram 400 for infection risk prediction using the system 110, according to an example embodiment of the present disclosure. Any of the components described above may be referred to hereinafter. The workflow diagram 400 may receive an input at block 402. The input may be received from the raw input component 302. The workflow diagram 400 may perform a content analysis at block 404. The content analysis may be implemented by the content analysis component 318 described above. The workflow diagram 400 may further include a CRAMP engine processing at block 406. The block 406 may represent processing performed at the CRAMP engine 320. The workflow diagram 400 may include a data visualization of block 408. The data visualization at block 408 may represent the data visualization 322 mentioned above.

Figure 5:
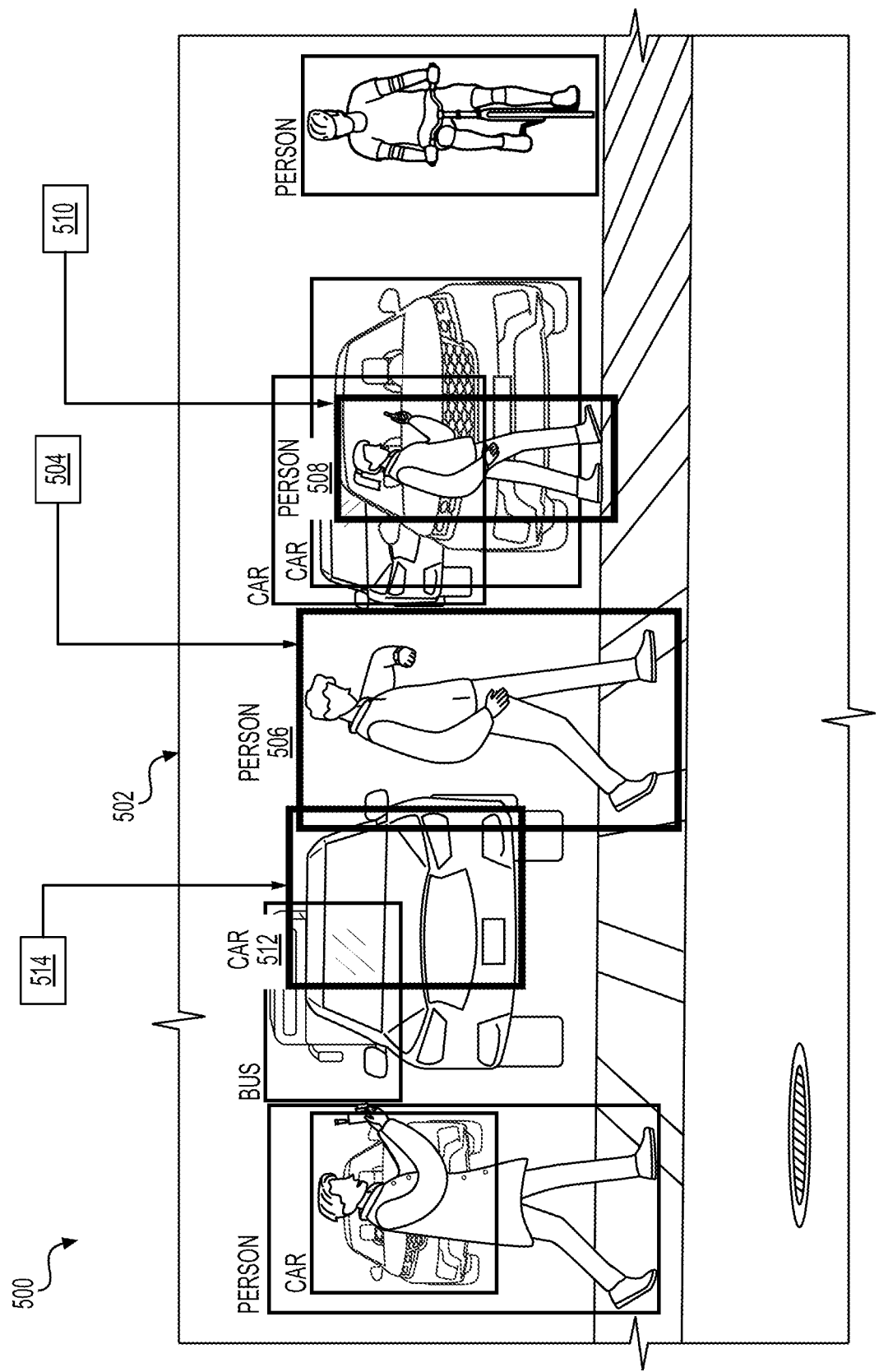
FIG. 5 illustrates a pictorial representation for vision-based tracking for the infection risk prediction using the virus risk prediction system, according to an example embodiment of the present disclosure.

FIG. 5 illustrates a pictorial representation 500 for vision-based tracking for virus risk prediction using a virus risk prediction system, according to an example embodiment of the present disclosure. Any of the components described above may be referred to hereinafter. The pictorial representation 500 illustrates a picture 502 with various objects detected therein. As mentioned above, the data collector 130 may detect objects for a geographic location 206. The objects identified from the picture 502 may be a car, a truck, a bicycle, a traffic light, a person, and the like. The picture 502 may further include a box 504 demarcating an object 506 (a person), a box 510 demarcating an object 508 (a person), and a box 514 demarcating an object 512 (a car.)The box 504, the box 510, and the box 514 may be bounding boxes. The box 504, the box 510, and the box 514 may mark the coordinates X, Y mentioned above of the calculation of the risk assessment score 230 for the object 506, the object 508, and the object 512. The extraction of spatial-temporal features for each of the objects 208 based on neural network-based feature extraction layers may be implemented on the box 504, the box 510, and the box 514. The data collector 130 may create the box 504, the box 510, and the box 514 so that to identify a single object through each box from the media. The data collector 130 may create multiple boxes like the box 504, the box 510, and the box 514 as illustrated to identify the objects 208. In an example, as illustrated the box 504 may coincide with the box 514 and include a part of the object 512 along with the main object 506 identified by the box 504. For example, in the picture 502, the box 504 may include the object 506 and a part of the object 512. The system 110 may not consider the part of the object 512 included in the box 504 as objects present in the coordinates X, Y.

Figure 6:
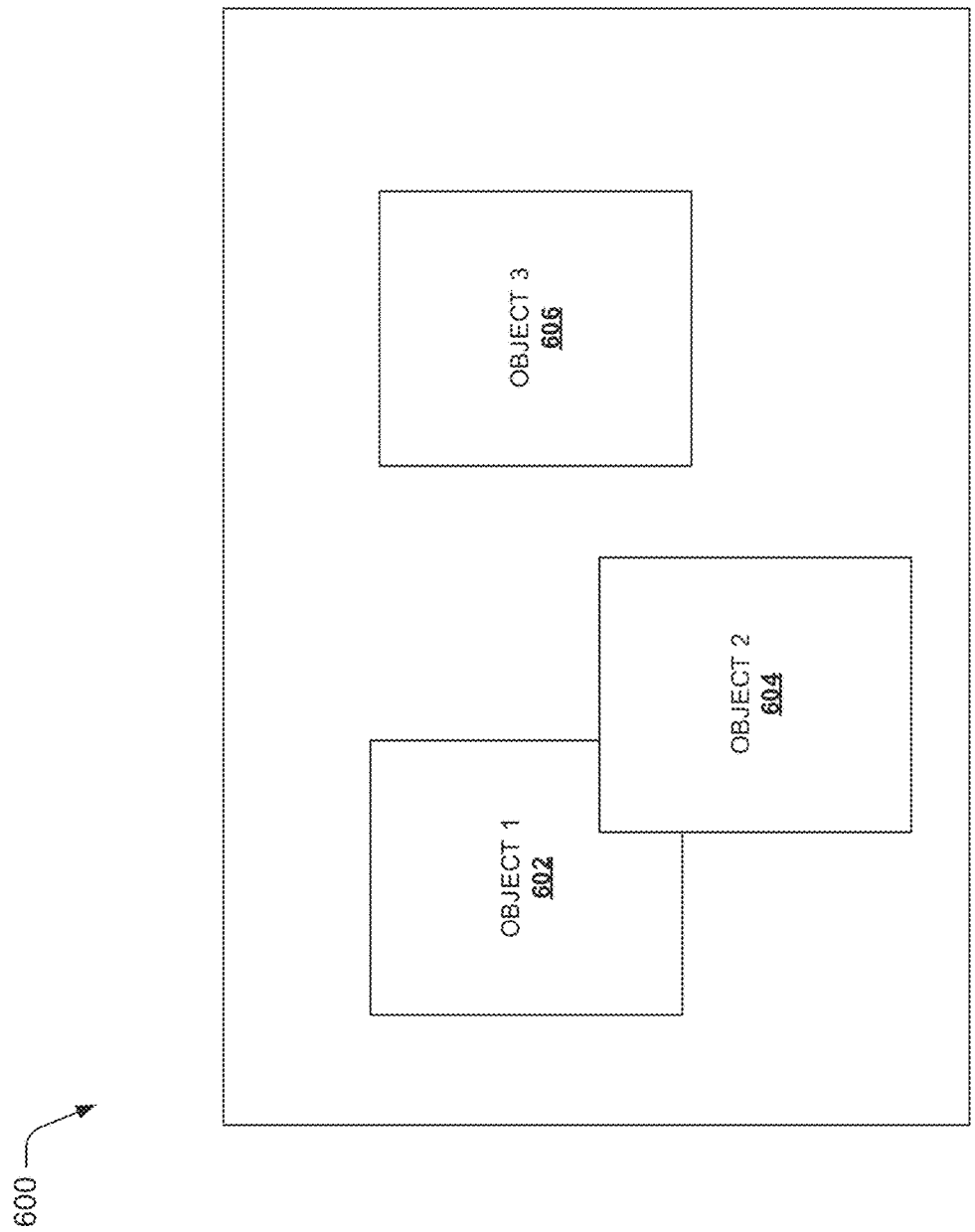
FIG. 6 schematically illustrates a plurality of objects detected across a geographical location for the infection risk prediction using the virus risk prediction system, according to an example embodiment of the present disclosure.

FIG. 6 illustrates a box representation 600 of the objects 208 detected across a geographical location for virus risk prediction using a virus risk prediction system, according to an example embodiment of the present disclosure. Any of the components described above may be referred to hereinafter. The box representation 600 illustrates an object 1 602, an object 2 604, and an object 3 606. The object 2 604 may be overlapping the object 1 602. The data collector 130 may detect the overlap with object 2 604 in the coordinates for the object 1 602. The data collector 130 may detect X, Y coordinates for the object 1-602, object 2-604, and the object 3-606.

Figure 7:
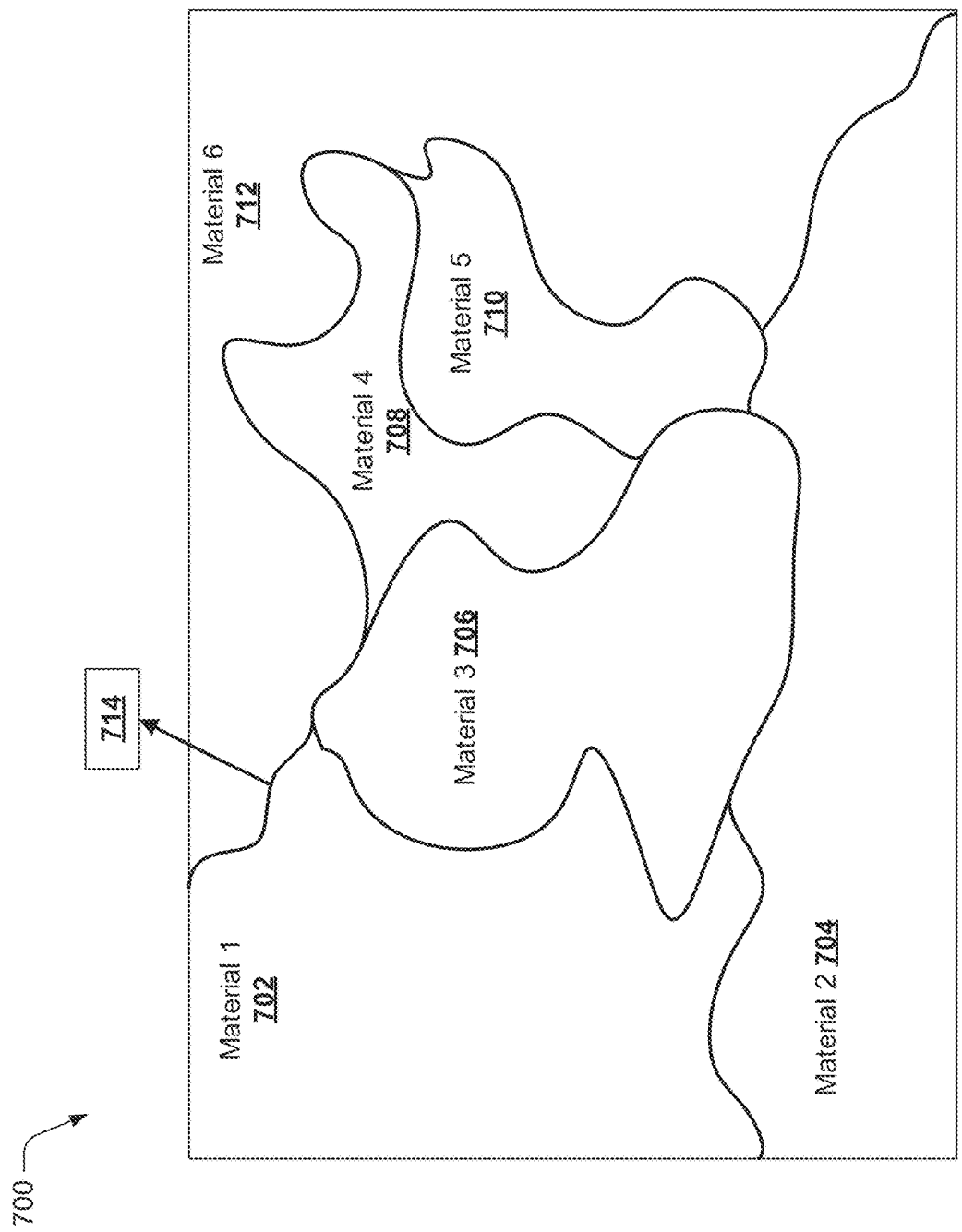
FIG. 7 illustrates a diagrammatic representation of a plurality of material categories for classifying a plurality of objects for the infection risk prediction using the infection risk prediction system, according to an example embodiment of the present disclosure.

FIG. 7 illustrates a diagrammatic representation 700 of the material categories 212 for classifying the objects 208 for virus risk prediction using the system 110, according to an example embodiment of the present disclosure. Any of the components described above may be referred to hereinafter. As mentioned above the material categories 212 may include the surface material 214 associated with the objects 208. The data collector 130 may implement techniques mentioned above for the detection of various surface material 214 associated with the objects 208.

The material categories 212 may be detected by the data collector 130 as mentioned by way of FIG. 2 in a continuous and integrated manner so that there may be no overlaps amongst the surface material 214 for multiple objects detected for the same image pixel. For example, a motorbike and a bike rider may be detected as objects present in the same image pixel. The image-based material detection techniques may detect the surface material 214 for each of the multiple objects in the same pixel by demarcating a material boundary 714 for each surface material. The material boundary 714 may detect the surface material for a part of the object present in the pixel frame. The material boundary 714 may provide integration and continuity of material detection across the image frame for the detection of various surface materials 214 present therein. material categories 212. For example, a material 1 702, a material 2-704, a material 3-706, a material 4-708, a material 5-710, and a material 6-712 may be detected in continuance with each other by the data collector 130.

FIG. 8 illustrates a heat map generation workflow 800 for infection risk prediction using the system 110, according to an example embodiment of the present disclosure.

The heat map generation workflow 800 may be deployed by the system 110 as an exemplary embodiment to generate the heat map 234. The heat map generation may include receiving an input from a media component 802. The media component 802 may include the media mentioned by way of FIGS. 1-3. The heat map generation 800 may further include training data 804. The training data 804 may include data for training a neural network model, such as the CNN model mentioned above. The training dataset may include, but is not limited to, training images, training image frames, the objects 208 detected from the training images, the surface material detection, and spatial-temporal features of the training images. The heat map generation 800 may include extraction of a set of spatial-temporal features 808 from the training data 804. The media 802 may comprise a set of multi-frames 806 that may be fed into a spatial-temporal model 810. The set of multi-frames 806 may be the plurality of image frames mentioned above. The set of multi-frames 806 may include a target frame for which the heat map 234 may need to be generated and a set of neighboring frames (as illustrated by FIG. 5). The spatial-temporal model 810 may also receive input from the set of spatial-temporal features 808. The spatial-temporal model 810 may extract one or more spatial-temporal features 210 of the set of multi-frames 806 based on the set of spatial-temporal features 808 and create a heat map 812 for the target frame based on the spatial-temporal features 210.

Figure 9:
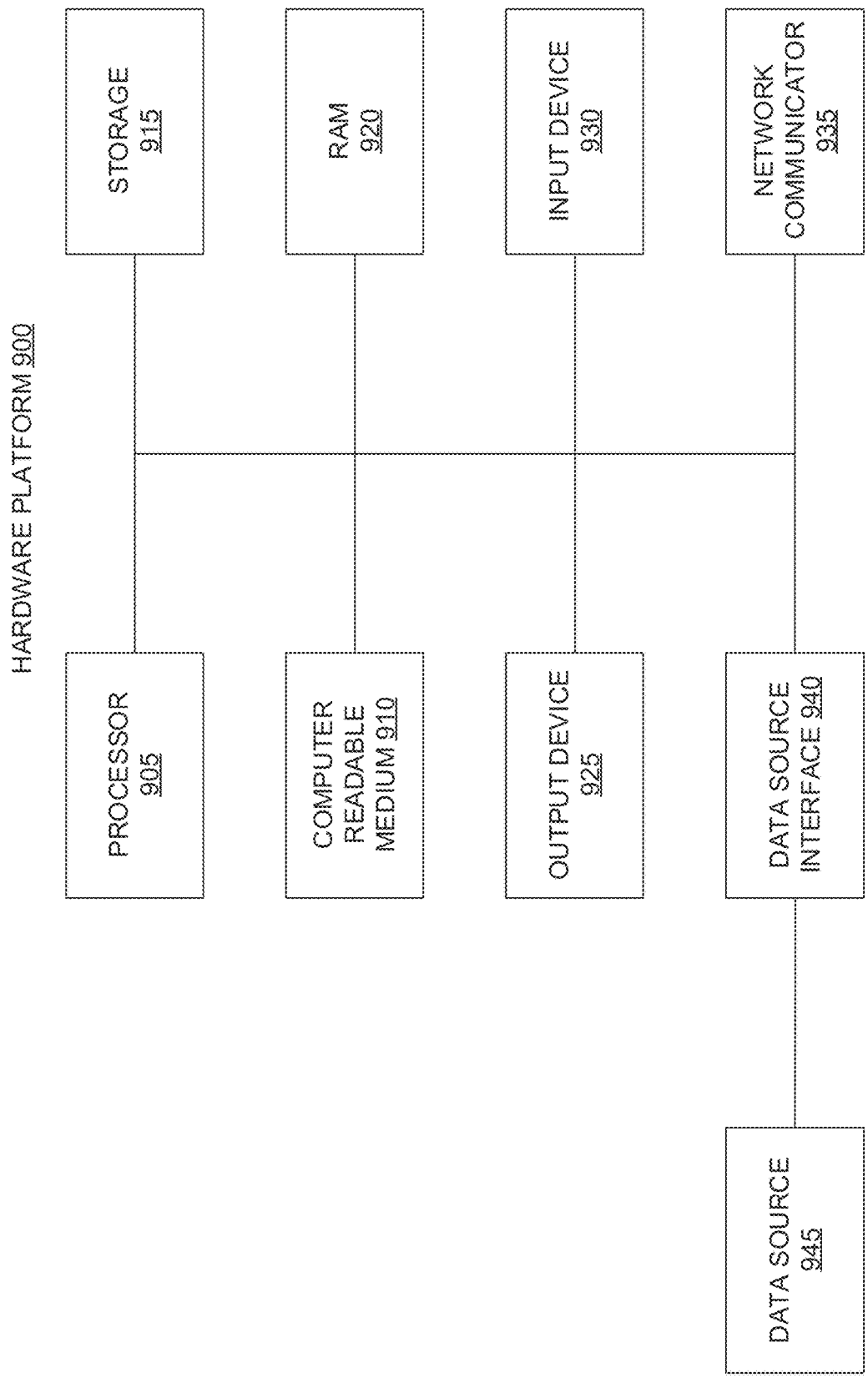
FIG. 9 illustrates a hardware platform for the implementation of the infection risk prediction system, according to an example embodiment of the present disclosure.

FIG. 9 illustrates a hardware platform 900 for implementation of the system 110, according to an example embodiment of the present disclosure. For the sake of brevity, construction and operational features of the system 110 which are explained in detail above are not explained in detail herein. Particularly, computing machines such as but not limited to internal/external server clusters, quantum computers, desktops, laptops, smartphones, tablets, and wearables which may be used to execute the system 110 or may have the structure of the hardware platform 900. The hardware platform 900 may include additional components not shown and that some of the components described may be removed and/or modified. In another example, a computer system with multiple GPUs can sit on external-cloud platforms including Amazon Web Services, or internal corporate cloud computing clusters, or organizational computing resources, etc.

The hardware platform 900 may be a computer system that may be used with the examples described herein. The computer system 900 may represent a computational platform that includes components that may be in a server or another computer system. The computer system 900 may execute, by a processor (e.g., a single or multiple processors) or other hardware processing circuit, the methods, functions and other processes described herein. These methods, functions and other processes may be embodied as machine-readable instructions stored on a computer-readable medium, which may be non-transitory, such as hardware storage devices (e.g., RAM (random access memory), ROM (read-only memory), EPROM (erasable, programmable ROM), EEPROM (electrically erasable, programmable ROM), hard drives, and flash memory). The computer system 900 may include a processor 905 that executes software instructions or code stored on a non-transitory computer-readable storage medium 910 to perform methods of the present disclosure. The software code includes, for example, instructions to gather data and documents and analyze documents. In an example, the data collector 130, the data analyzer 140, and the modeler 150 may be software codes or components performing these steps.

The instructions on the computer-readable storage medium 910 are read and stored the instructions in storage 915 or in random access memory (RAM) 920. The storage 915 provides a large space for keeping static data where at least some instructions could be stored for later execution. The stored instructions may be further compiled to generate other representations of the instructions and dynamically stored in the RAM 920. The processor 905 reads instructions from the RAM 920 and performs actions as instructed.

The computer system 900 further includes an output device 925 to provide at least some of the results of the execution as output including, but not limited to, visual information to users, such as external agents. The output device can include a display on computing devices and virtual reality glasses. For example, the display can be a mobile phone screen or a laptop screen. GUIs and/or text are presented as an output on the display screen. The computer system 900 further includes input device 930 to provide a user or another device with mechanisms for entering data and/or otherwise interact with the computer system 900. The input device may include, for example, a keyboard, a keypad, a mouse, or a touchscreen. Each of these output devices 925 and input devices 930 could be joined by one or more additional peripherals. In an example, the output device 925 may be used to display the results of the query 202. The output device 925 may be used to display the heat map 234 for the geographic location 206 based on the spatial-temporal features 210 for each of the objects 208 and the risk assessment score 230 for each of the objects 208.

A network communicator 935 may be provided to connect the computer system 900 to a network and in turn to other devices connected to the network including other clients, servers, data stores, and interfaces, for instance. A network communicator 935 may include, for example, a network adapter such as a LAN adapter or a wireless adapter. The computer system 900 includes a data source interface 940 to access data source 945. A data source is an information resource. As an example, a database of exceptions and rules may be a data source. Moreover, knowledge repositories and curated data may be other examples of data sources.

Figure 10A:
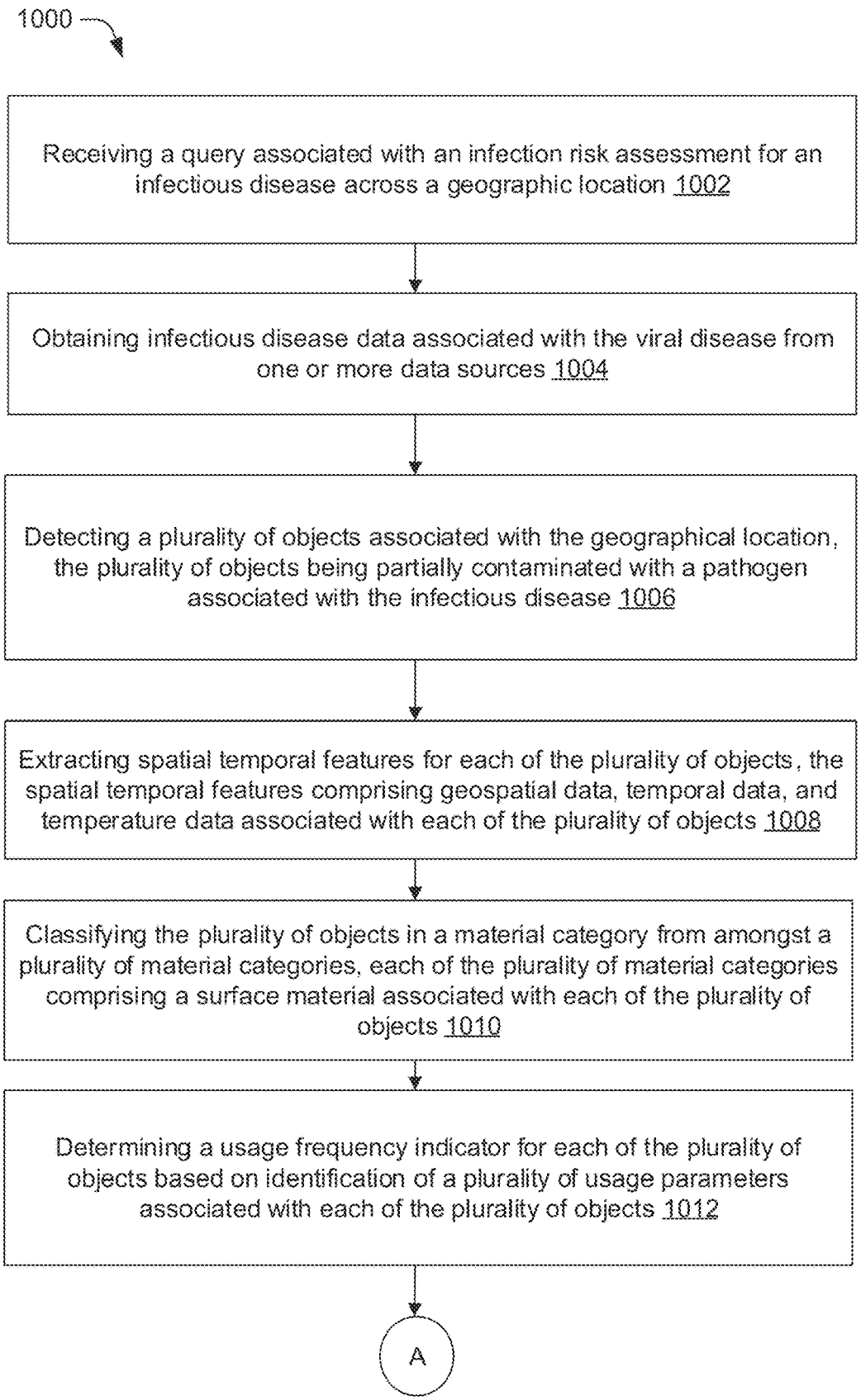
FIGS. 10A and 10B illustrate a process flowchart for the infection risk prediction, according to an example embodiment of the present disclosure.
Figure 10B:
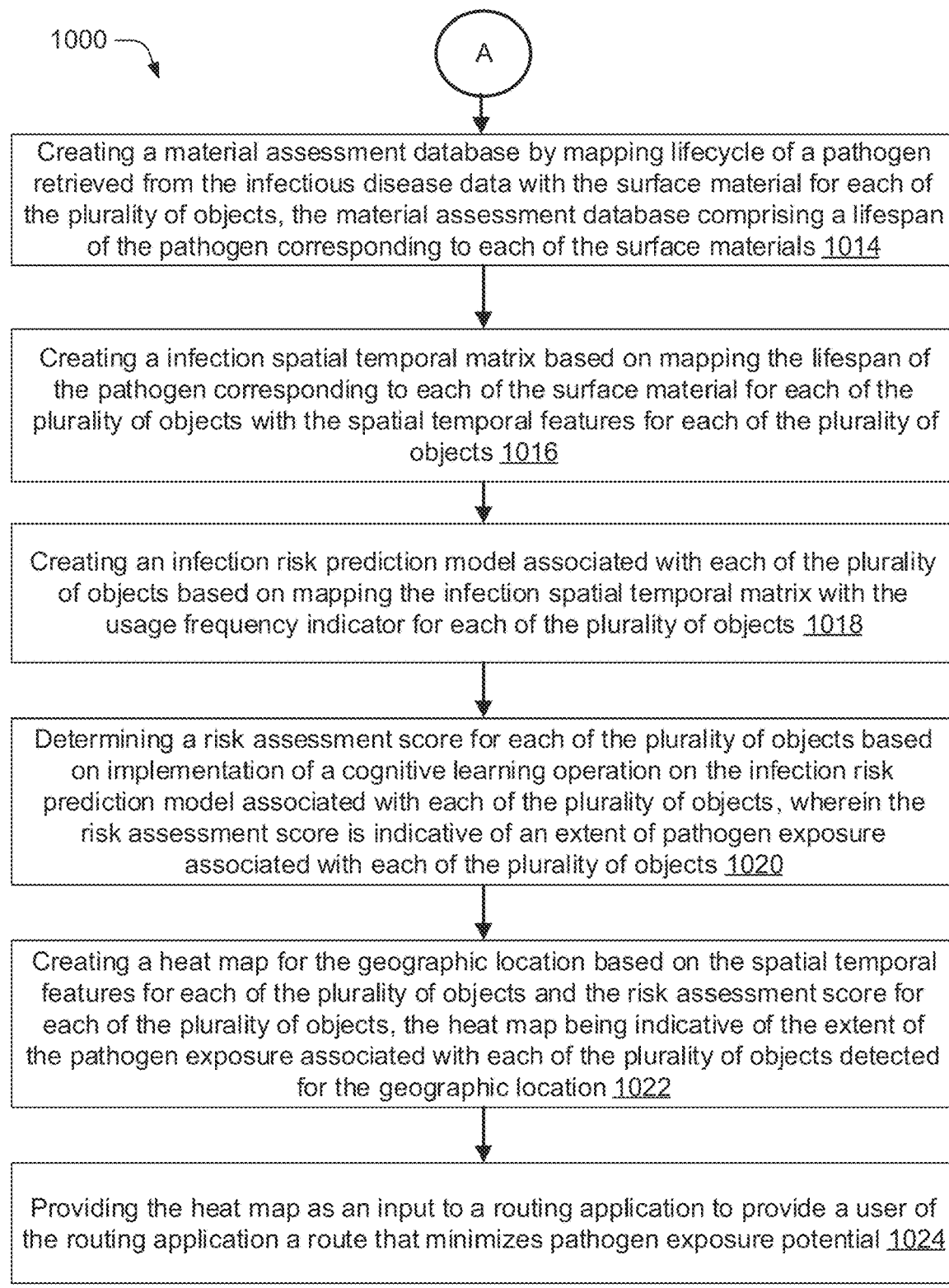

FIGS. 10A and 10B illustrate a process flowchart for infection risk prediction using the system 110, according to an example embodiment of the present disclosure. It should be understood that method steps are shown here for reference only and other combinations of the steps may be possible. Further, the method 1000 may contain some steps in addition to the steps shown in FIGS. 10A and 10B. For the sake of brevity, construction, and operational features of the system 110 which are explained in detail in the description of FIGS. 1-9 are not explained in detail in the description of FIGS. 10A and 10B. The method 1000 may be performed by a component of the system 110.

At block 1002, a query 202 associated with an infection risk assessment for an infectious disease, such as the viral disease 204 across a geographic location 206, may be received. In an example embodiment, the viral disease 204 associated with the query 202 may be a severe acute respiratory syndrome coronavirus 2 (SARS-CoV-2).

At block 1004, infectious disease data may be obtained associated with the infectious disease from one or more data sources.

At block 1006, the plurality of objects 208 associated with the geographical location may be detected. The plurality of objects 208 may be potentially contaminated with a pathogen, such as a virus associated with the viral disease 204.

At block 1008, spatial-temporal features 210 may be extracted for each of the plurality of objects 208. The spatial-temporal features 210 may comprise one or more of geospatial data, temporal data, and temperature data associated with each of the plurality of objects 208.

At block 1010, the plurality of objects 208 may be classified in a material category from amongst a material categories 212. Each of the material categories 212 may comprise a surface material 214 associated with each of the plurality of objects 208. The method 1000 may determine the material categories 212 based on an analysis of a reflectance attribute associated with the surface material 214 associated with each of the plurality of objects 208. The method 1000 may include an analysis of a plurality of material attributes associated with the surface material 214 associated with each of the plurality of objects 208 for determining the material categories 212.

At block 1012, the usage frequency indicator 216 may be determined for each of the plurality of objects 208 based on the identification of a plurality of usage parameters 218 associated with each of the plurality of objects 208. In an example embodiment, the method 1000 may include determining a unique usage frequency indicator 216 for a user based on the identification of the plurality of usage parameters 218 unique to the user.

At block 1014, the material assessment database 220 may be created, the material assessment database may include details pertaining to a lifespan of the pathogen or the virus with respect to each of the plurality of material categories.

At block 1016, the infection spatial-temporal matrix 226 may be created based on mapping the lifespan of the pathogen corresponding to each of the surface material 214 for each of the plurality of objects 208 with the spatial-temporal features 210 for each of the plurality of objects 208.

At block 1018, the infection risk prediction model 228 may be created associated with each of the plurality of objects 208 based on mapping the infection spatial-temporal matrix 226 with the usage frequency indicator 216 for each of the plurality of objects 208.

At block 1020, the risk assessment score 230 may be determined for each of the plurality of objects 208 based on the implementation of a cognitive learning operation 232 on the infection risk prediction model 228 associated with each of the plurality of objects 208. The risk assessment score 230 may be indicative of an extent of pathogen exposure associated with each of the plurality of objects 208.

At block 1022, the heat map 234 may be created for the geographic location 206 based on the spatial-temporal features 210 for each of the plurality of objects 208 and the risk assessment score 230 for each of the plurality of objects 208 The heat map 234 may be indicative of the extent of the pathogen exposure associated with each of the plurality of objects 208 detected for the geographic location 206.

Following the creation of the heat map 234, at block 1024, the heat map 234 may be displayed to a user or provided as an input to an application for consumption by a user. For example, the heat map 234 may be provided as a visualization to the user that is overlaid on a live camera view on a display of the user's mobile device. In another example embodiment, the heat map 234 may be provided as an input to a routing application on the user's mobile device that may select from a plurality of routes and recommend to the user, based on the heat map 234, a route that minimizes potential pathogen exposure and/or has a least likely pathogen exposure potential. In an example embodiment, the method 1000 may further comprise detecting the plurality of objects 208 from an image, a video-based medium, a uniform resource locator, a geolocation, and a data stream associated with the geographic location 206. The method 1000 may comprise extracting a plurality of image frames from the image, the video-based medium, the uniform resource locator, the geolocation, and the data stream associated with the geographic location 206. The method 1000 may comprise extracting the spatial-temporal features 210 for each of the plurality of objects 208 based on neural network-based feature extraction layers implemented on the plurality of image frames.

The method 1000 may further comprise generating the cleaning alert for a user for an object, from among the plurality of objects 208, having the risk assessment score 230 above a threshold risk assessment score.

In an example, the method 1000 may be practiced using a non-transitory computer-readable medium. In an example, the method 1000 may be computer-implemented.

The present disclosure provides for the system 110 that may generate key insights related to virus risk prediction with minimal human intervention.

One of ordinary skill in the art will appreciate that techniques consistent with the present disclosure are applicable in other contexts as well without departing from the scope of the disclosure.

What has been described and illustrated herein are examples of the present disclosure. The terms, descriptions, and figures used herein are set forth by way of illustration only and are not meant as limitations. Many variations are possible within the spirit and scope of the subject matter, which is intended to be defined by the following claims and their equivalents in which all terms are meant in their broadest reasonable sense unless otherwise indicated.

We claim:
1. A system comprising:
a processor;
memory storing executable instructions, which, when executed by the processor cause the system to:
receive a query associated with a risk assessment for an infectious disease across a geographic location;
obtain infectious disease data associated with the infectious disease from a plurality of data sources;
detect a plurality of objects associated with the geographical location, the plurality of objects being potentially contaminated with a pathogen associated with the infectious disease;
extract spatial-temporal features for each of the plurality of objects, the spatial-temporal features comprising at least one of geospatial data, temporal data, and temperature data associated with each of the plurality of objects, wherein, to extract the spatial-temporal features, the processor is to:
extract a plurality of image frames from at least one of an image, a video-based medium, information associated a uniform resource locator, and a data stream associated with the geographic location, and
obtain the spatial-temporal features for each of the plurality of objects based on neural network-based feature extraction layers implemented on the plurality of image frames;
classify the plurality of objects in a material category from amongst a plurality of material categories, the material category indicative of a surface material associated with each of the plurality of objects;
determine a usage frequency indicator for each of the plurality of objects based on identification of a plurality of usage parameters associated with each of the plurality of objects;
create a material assessment database including details pertaining to a lifespan of the pathogen with respect to each of the plurality of material categories;
create an infection spatial-temporal matrix based on mapping the lifespan of the pathogen corresponding to each of the surface materials for the plurality of objects with the spatial-temporal features for each of the plurality of objects;
create a risk prediction model associated with each of the plurality of objects based on mapping the infection spatial-temporal matrix with the usage frequency indicator for each of the plurality of objects;
determine a risk assessment score for each of the plurality of objects based on implementation of a cognitive learning operation on the risk prediction model associated with each of the plurality of objects, wherein the risk assessment score is indicative of an extent of pathogen exposure associated with each of the plurality of objects;
create a heat map for the geographic location based on the spatial-temporal features for each of the plurality of objects and the risk assessment score for each of the plurality of objects, the heat map being indicative of the extent of the pathogen exposure associated with each of the plurality of objects detected for the geographic location.

2. The system as claimed in claim 1, wherein the processor detects the plurality of objects from the image, the video-based medium, the information associated with the uniform resource locator, and the data stream associated with the geographic location.

3. The system as claimed in claim 1, wherein the processor generates a cleaning alert for a user for an object, from among the plurality of objects, having the risk assessment score above a threshold risk assessment score.

4. The system as claimed in claim 1, wherein the viral disease associated with the query is a severe acute respiratory syndrome coronavirus 2 (SARSSARS-COV-2).

5. The system as claimed in claim 1, wherein the processor determines the plurality of material categories based on:
an analysis of a reflectance attribute associated with the surface material associated with each of the plurality of objects; and
an analysis of a plurality of material attributes associated with the surface material associated with each of the plurality of objects.

6. The system as claimed in claim 1, wherein the processor determines a unique usage frequency indicator for a user based on identification of the plurality of usage parameters unique to the user.

7. The system as claimed in claim 1, wherein the processor is further to provide the heat map as an input to a routing application to provide a user of the routing application a route that minimizes exposure to the pathogen.

8. A method comprising:
receiving, by a processor a query associated with a risk assessment for an infectious disease across a geographic location;
obtaining, by the processor infectious disease data associated with the infectious disease from a plurality of data sources;
detecting, by the processor, a plurality of objects associated with the geographical location, the plurality of objects being potentially contaminated with a pathogen associated with the infectious disease;
extracting, by the processor, spatial-temporal features for each of the plurality of objects, the spatial-temporal features comprising at least one of geospatial data, temporal data, and temperature data associated with each of the plurality of objects, wherein the extracting spatial-temporal features comprises:

extracting a plurality of image frames from at least one of an image, a video-based medium, information associated a uniform resource locator, and a data stream associated with the geographic location, and obtaining the spatial-temporal features for each of the plurality of objects based on neural network-based feature extraction layers implemented on the plurality of image frames;

classifying, by the processor, the plurality of objects in a material category from amongst a plurality of material categories, the material category indicative of a surface material associated with each of the plurality of objects;

determining, by the processor, a usage frequency indicator for each of the plurality of objects based on identification of a plurality of usage parameters associated with each of the plurality of objects;

creating, by the processor, a material assessment database including details pertaining to a lifespan of the pathogen with respect to each of the plurality of material categories;

creating, by the processor, an infection spatial-temporal matrix based on mapping the lifespan of the pathogen corresponding to each of the surface materials for the plurality of objects with the spatial-temporal features for each of the plurality of objects;

creating, by the processor, a risk prediction model associated with each of the plurality of objects based on mapping the infection spatial-temporal matrix with the usage frequency indicator for each of the plurality of objects;

determining, by the processor, a risk assessment score for each of the plurality of objects based on implementation of a cognitive learning operation on the risk prediction model associated with each of the plurality of objects, wherein the risk assessment score is indicative of an extent of pathogen exposure associated with each of the plurality of objects; and creating, by the processor, a heat map for the geographic location based on the spatial-temporal features for each of the plurality of objects and the risk assessment score for each of the plurality of objects, the heat map being indicative of the extent of the pathogen exposure associated with each of the plurality of objects detected for the geographic location.

9. The method as claimed in claim 8, wherein the method further comprises generating, by the processor, a cleaning alert for a user for an object, from among the plurality of objects, having the risk assessment score above a threshold risk assessment score.

10. The method as claimed in claim 8, wherein determining the plurality of material categories is based on:
an analysis of a reflectance attribute associated with the surface material associated with each of the plurality of objects; and
an analysis of a plurality of material attributes associated with the surface material associated with each of the plurality of objects.

11. The method as claimed in claim 8, wherein the method further comprises determining, by the processor, a unique usage frequency indicator for a user based on identification of the plurality of usage parameters unique to the user.

12. The method as claimed in claim 8, wherein the method further comprises providing, by the processor, the heat map as an input to a routing application to provide a user of the routing application a route that minimizes exposure to the pathogen.

13. A non-transitory computer readable medium comprising machine executable instructions that are executable by a processor to:
receive a query associated with a risk assessment for an infectious disease across a geographic location;
obtain infectious disease data associated with the infectious disease from a plurality of data sources;
detect a plurality of objects associated with the geographical location, the plurality of objects being potentially contaminated with a pathogen associated with the infectious disease;
extract spatial-temporal features for each of the plurality of objects, the spatial-temporal features comprising at least one of geospatial data, temporal data, and temperature data associated with each of the plurality of objects, wherein, to extract the spatial-temporal features, the processor is to:
extract a plurality of image frames from at least one of an image, a video-based medium, information associated a uniform resource locator, and a data stream associated with the geographic location, and
obtain the spatial-temporal features for each of the plurality of objects based on neural network-based feature extraction layers implemented on the plurality of image frames;
classify the plurality of objects in a material category from amongst a plurality of material categories, the material category indicative of a surface material associated with each of the plurality of objects;
determine a usage frequency indicator for each of the plurality of objects based on identification of a plurality of usage parameters associated with each of the plurality of objects;
create a material assessment database including details pertaining to a lifespan of the pathogen with respect to each of the plurality of material categories;
create an infection spatial-temporal matrix based on mapping the lifespan of the pathogen corresponding to each of the surface materials for the plurality of objects with the spatial-temporal features for each of the plurality of objects;
create a risk prediction model associated with each of the plurality of objects based on mapping the infection spatial-temporal matrix with the usage frequency indicator for each of the plurality of objects;
determine a risk assessment score for each of the plurality of objects based on implementation of a cognitive learning operation on the risk prediction model associated with each of the plurality of objects, wherein the risk assessment score is indicative of an extent of pathogen exposure associated with each of the plurality of objects; and
create a heat map for the geographic location based on the spatial-temporal features for each of the plurality of objects and the risk assessment score for each of the plurality of objects, the heat map being indicative of the extent of the pathogen exposure associated with each of the plurality of objects detected for the geographic location.

14. The non-transitory computer readable medium of claim 13 including machine executable instructions, that are executable by the processor to further generate a cleaning alert for a user for an object, from among the plurality of objects, having the risk assessment score above a threshold risk assessment score.

15. The non-transitory computer readable medium of claim 13 including machine executable instructions, that are executable by the processor to determine the plurality of material categories based on:
- an analysis of a reflectance attribute associated with the surface material associated with each of the plurality of objects; and
- an analysis of a plurality of material attributes associated with the surface material associated with each of the plurality of objects.

16. The non-transitory computer readable medium of claim 13 including machine executable instructions, that are executable by the processor to determine a unique usage frequency indicator for a user based on identification of the plurality of usage parameters unique to the user.

17. The non-transitory computer readable medium of claim 13 including machine executable instructions, that are executable by the processor to provide the heat map as an input to a routing application to provide a user of the routing application a route that minimizes exposure to the pathogen.

* * * * *